United States Patent [19]
Thompson et al.

[11] Patent Number: 6,030,402
[45] Date of Patent: Feb. 29, 2000

[54] APPARATUS AND METHODS FOR THE PENETRATION OF TISSUE, AND THE CREATION OF AN OPENING THEREIN

[76] Inventors: Ronald J. Thompson, 110 Stanbery Ridge, Ft. Thomas, Ky. 41075; Jack B. Stubbs, 4266 Laura Marie Dr., Waynesville, Ohio 45068

[21] Appl. No.: 09/065,254

[22] Filed: Apr. 23, 1998

[51] Int. Cl.[7] ................................................ A61B 17/34
[52] U.S. Cl. ........................ 606/185; 606/167; 606/164; 606/232; 606/105
[58] Field of Search .................................. 606/185, 167, 606/170, 181, 182, 183, 184, 105, 232; 604/164

[56] References Cited

U.S. PATENT DOCUMENTS

| | | |
|---|---|---|
| 3,577,991 | 5/1971 | Wilkinson . |
| 3,831,585 | 8/1974 | Brondy et al. ........................ 606/185 |
| 4,592,356 | 6/1986 | Gutierrez ............................. 606/185 |
| 4,684,369 | 8/1987 | Wildemeersch . |
| 4,762,519 | 8/1988 | Frimberger . |
| 4,826,481 | 5/1989 | Sacks et al. . |
| 4,869,717 | 9/1989 | Adair . |
| 5,066,280 | 11/1991 | Braithwaite . |
| 5,112,310 | 5/1992 | Grobe . |
| 5,116,353 | 5/1992 | Green . |
| 5,152,749 | 10/1992 | Giesy et al. . |
| 5,158,543 | 10/1992 | Lazarus . |
| 5,167,627 | 12/1992 | Clegg et al. . |
| 5,215,526 | 6/1993 | Deniega et al. . |
| 5,271,380 | 12/1993 | Riek et al. . |
| 5,300,036 | 4/1994 | Mueller et al. . |
| 5,318,585 | 6/1994 | Guy et al. . |
| 5,330,497 | 7/1994 | Freitas et al. ........................ 606/185 |
| 5,334,150 | 8/1994 | Kaali . |
| 5,342,382 | 8/1994 | Brinkerhoff et al. . |
| 5,343,874 | 9/1994 | Picha et al. . |
| 5,348,541 | 9/1994 | Lyell . |
| 5,356,382 | 10/1994 | Picha et al. ........................ 606/105 |
| 5,366,445 | 11/1994 | Haber et al. . |
| 5,370,625 | 12/1994 | Schichman . |
| 5,372,588 | 12/1994 | Farley et al. ........................ 606/167 |
| 5,397,325 | 3/1995 | Della Badia et al. . |
| 5,399,167 | 3/1995 | Deniega . |
| 5,407,427 | 4/1995 | Zhu et al. . |
| 5,431,676 | 7/1995 | Dubrul et al. . |
| 5,454,791 | 10/1995 | Tovey et al. . |
| 5,624,459 | 4/1997 | Kortenbach et al. ................. 606/185 |
| 5,690,663 | 11/1997 | Stephens . |
| 5,690,664 | 11/1997 | Sauer et al. . |
| 5,707,362 | 1/1998 | Yoon . |
| 5,713,869 | 2/1998 | Morejon . |
| 5,725,553 | 3/1998 | Moenning . |
| 5,728,110 | 3/1998 | Vidal et al. . |
| 5,843,115 | 12/1998 | Morejon ............................. 606/185 |

*Primary Examiner*—Michael Buiz
*Assistant Examiner*—(Jackie)Tan-Uyen T. Ho
*Attorney, Agent, or Firm*—Dinsmore & Shohl LLP

[57] ABSTRACT

An instrument for the penetration of tissue, including a backstop assembly having a shaft and a backstop; and a penetration member slidingly engaged with the backstop shaft, and configured for penetrating tissue. The backstop assembly and the penetration member are configured such that the backstop may be positioned adjacent tissue to be penetrated, such that as the penetration member is urged through the tissue along the backstop shaft, the backstop will limit the depth of penetration of the penetration member through the tissue. A method of using this instrument is also provided.

39 Claims, 18 Drawing Sheets

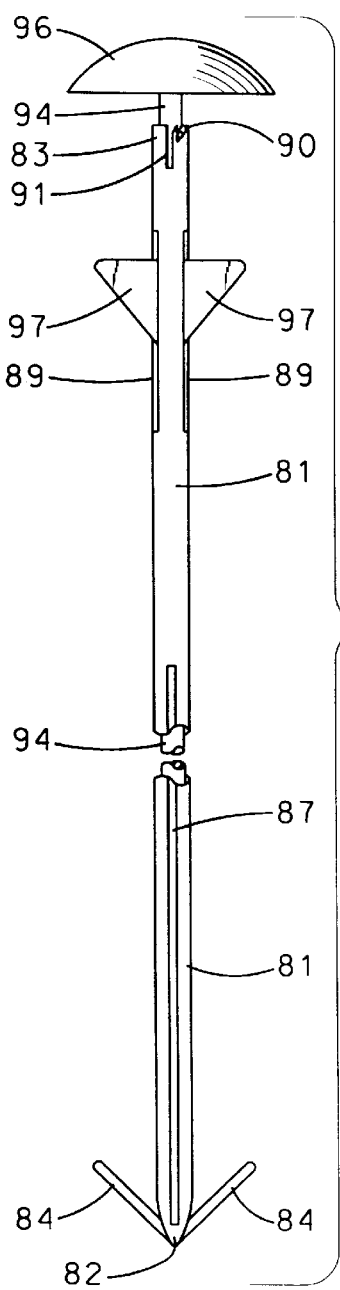
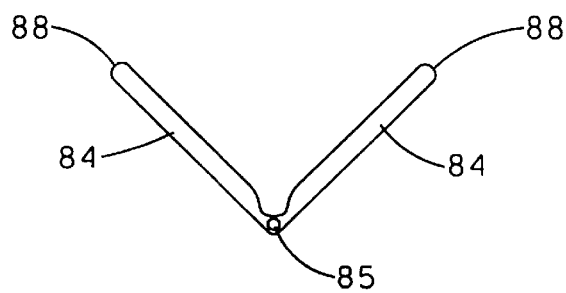
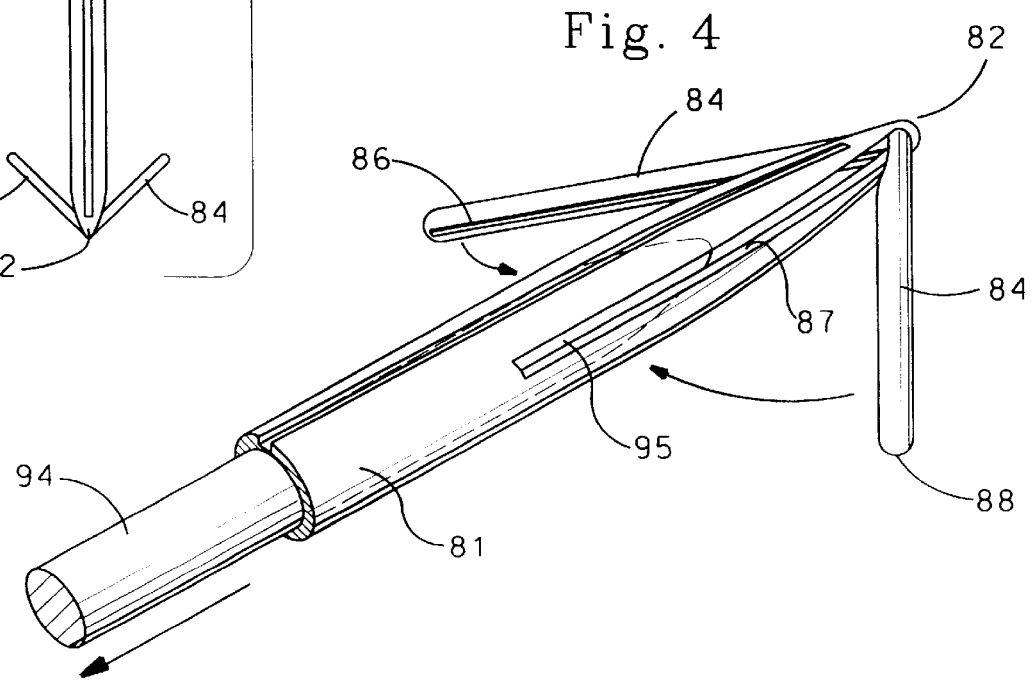

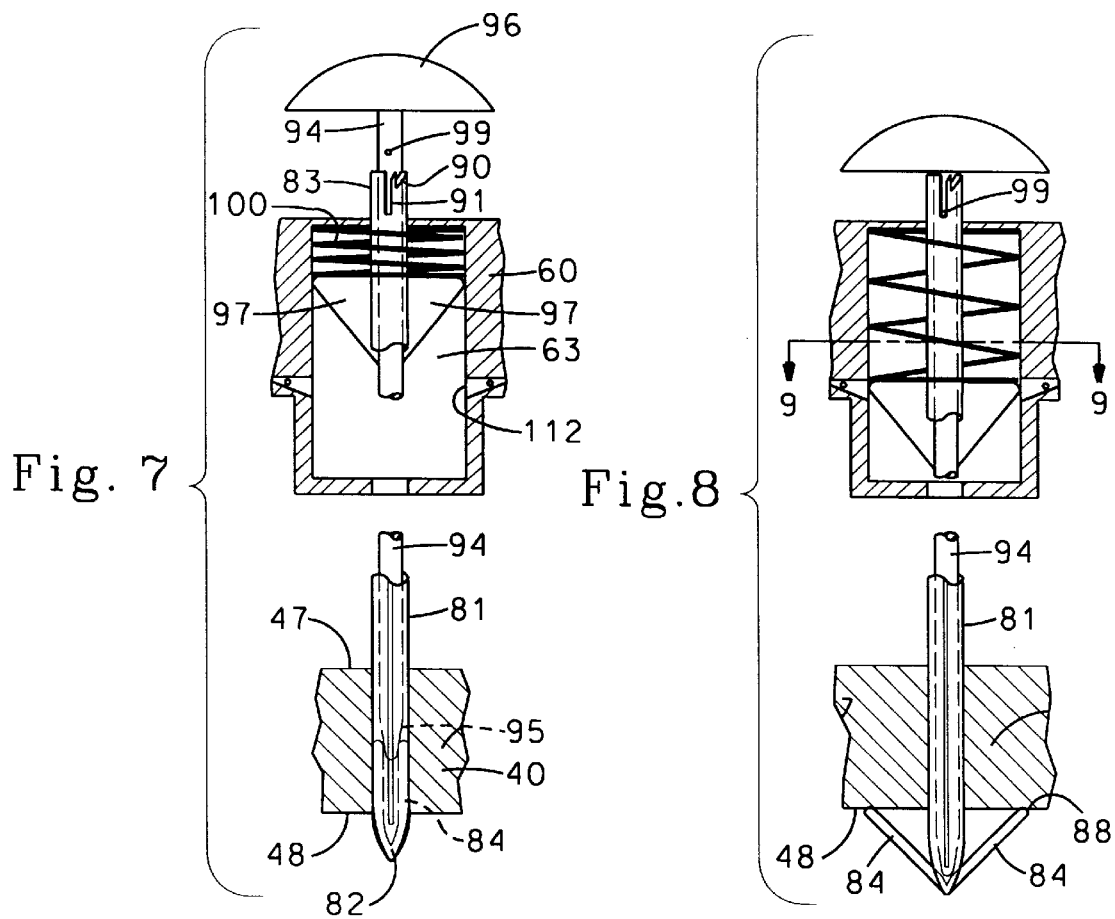
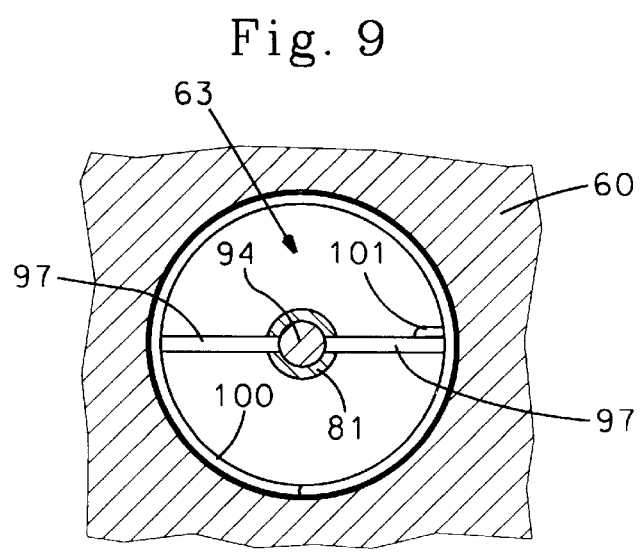

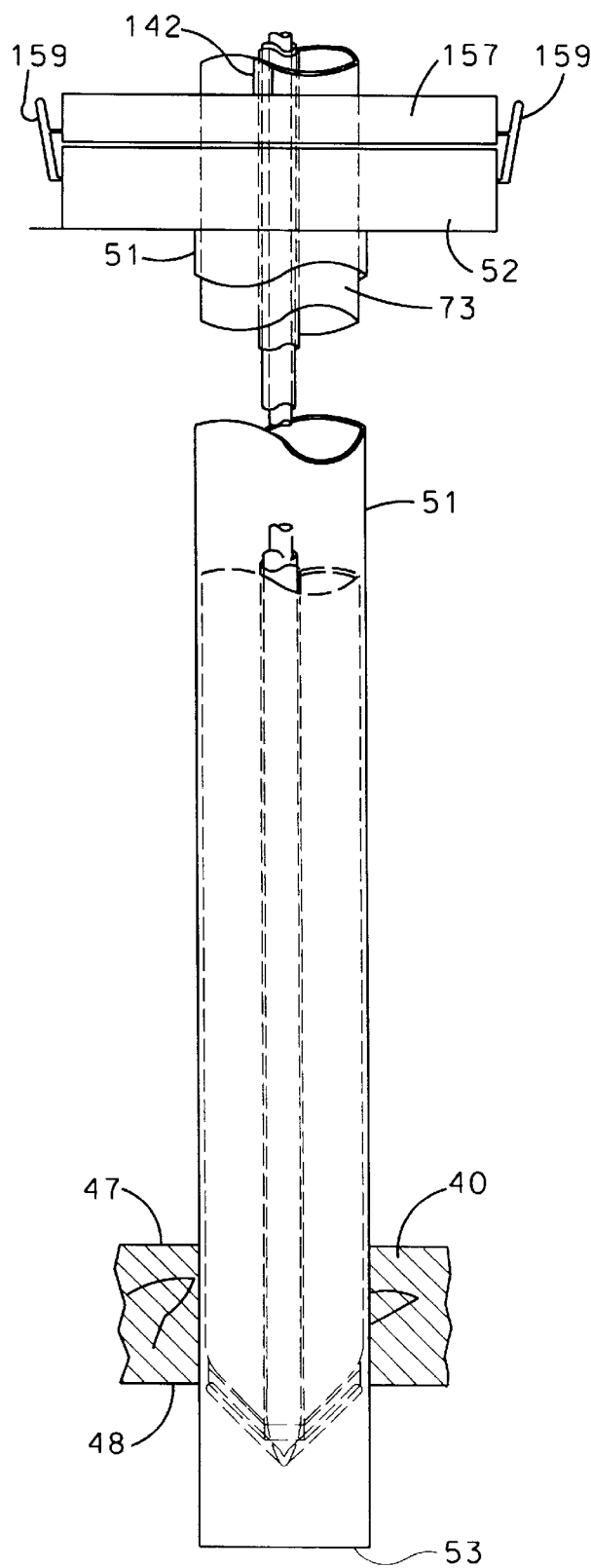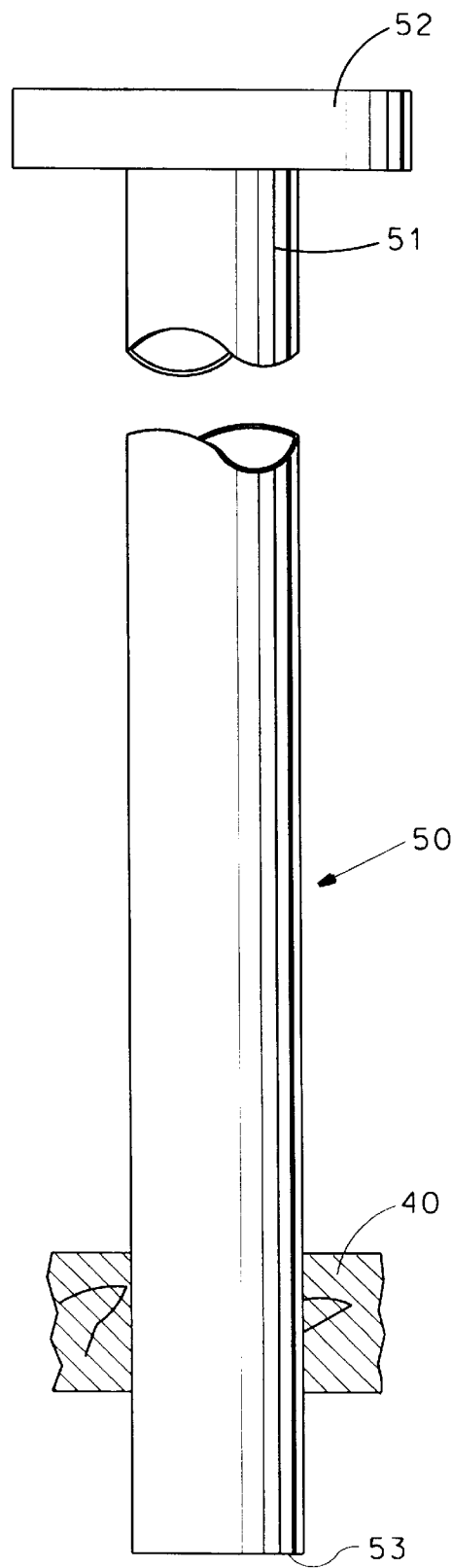
Fig. 22
Fig. 23

APPARATUS AND METHODS FOR THE PENETRATION OF TISSUE, AND THE CREATION OF AN OPENING THEREIN

BACKGROUND OF THE INVENTION

1. Field of the Invention

The present invention is directed towards apparatus and methods for penetrating tissue and creating openings therein in order to provide access to the interior of a patient's body. The present invention provides apparatus and methods which are particularly suited for creating openings which provide access to anatomical cavities, either directly through the opening itself or through a cannula positioned within the tissue opening. One embodiment of the present invention comprises a trocar.

2. Description of Related Art

Various medical procedures require the penetration of tissue to provide access to the interior of the patient's body. This is particularly true, for example, of endoscopic procedures wherein an opening in tissue must first be created to provide access to anatomical cavities or other internal structures. As used herein, "endoscopic" refers to procedures which employ tubular optical instruments (i.e., endoscopes) which are inserted into a patient to provide vision therein. The endoscope also typically has a hollow cannula through which other instruments may be inserted into the patient. The term "endoscopic" is generic to, and therefore includes, terms such as "laparascopic" and "arthroscopic" which refer to the use of an endoscope in a particular region of the body. Typically, a cannula is positioned within the tissue opening, and various medical instruments (such as an endoscope) may then be passed through the cannula into the interior of the patient.

One commonly-employed instrument for penetrating tissue is referred to as a trocar, and generally comprises a cutting assembly (or obturator) and an outer cannula (also referred to as the trocar tube or sleeve). The cannula is positioned against the patient's skin, and the cutting assembly is positioned within the interior of the cannula. The sharp distal end of the cutting assembly is then urged through the skin until it enters the anatomical cavity being penetrated. The cannula is then urged through the tissue opening created by the cutting assembly, and the cutting assembly is thereafter withdrawn. The cannula remains in place, and provides a passageway through which access to the anatomical cavity is provided.

Urging the cutting assembly of a trocar, or, for that matter, any other sharp instrument, through tissue can be dangerous if not performed properly. Blood vessels, organs and other delicate structures within the patient's body can be inadvertently damaged by the cutting assembly. Even more problematic is the fact that such inadvertent damage can go initially undetected, thereby leading to further complications. In fact, injury to major blood vessels, particularly in the abdomen, has become more common as the use of endoscopes has increased. Unfortunately, such vascular injuries often prove fatal, particularly if they go undetected for a significant period of time.

Various techniques and apparatus have been developed in order to reduce the risk associated with trocars. For example, a hollow needle (commonly referred to as a Veres needle) may be inserted into the abdomen, and a gas introduced therethrough in order to insufflate the abdomen. Insufflation causes a tenting-up of the abdomen, which tends to reduce the potential for over-insertion of the cutting blade. Vascular damage can and still does occur, however, and improper insertion of the insufflation needle has even been known to cause serious injury or death.

Numerous types of "safety trocars" have also been developed, wherein a spring-loaded shield helps prevent inadvertent damage caused by the cutting tip. The shield retracts away from the tip as the cutting blade is urged through the tissue. Once the cutting blade has passed into the anatomical cavity and the tissue is no longer bearing against the shield, the shield springs forward to cover the cutting blade. Such trocars are described, for example, in U.S. Pat. Nos. 5,116,353, 5,215,526, and 5,707,362. Even such "safety trocars," however, are not foolproof, and trocar injuries and deaths have continued to rise even as the use of these safety trocars has become more widespread.

Unfortunately, more and more endoscopic surgical procedures are developed each year. For example, gallbladder removal (referred to as a cholecystectomy), which once required a large abdominal incision and several days of in-hospital recovery, may now be performed laparascopically through a small umbilical incision on an out-patient basis. Not surprisingly, patient demand for such procedures has also increased significantly, due to their minimally-invasive nature, reduced post-operative recovery time, and lower cost.

The development of improved endoscopes has also provided physicians with a minimally-invasive means for direct examination of the interior of a patient. The result is that many patients, particularly those suffering from certain forms of cancer, are subjected to multiple examinations and procedures by means of an endoscope. In fact, some cancer patients undergo multiple laparoscopic procedures over a short period of time. Unfortunately, the increased frequency of these procedures greatly increases the risk of injury or death associated with trocar insertion. Thus, there is a need for apparatus and methods which will decrease the possibility of inadvertent patient injury during tissue penetration, particularly during cannula insertion of endoscopic procedures.

BRIEF DESCRIPTION OF THE DRAWINGS

While the specification concludes with claims particularly pointing out and distinctly claiming applicants' invention, it is believed that the same will be better understood from the following description taken in conjunction with the accompanying drawings in which:

FIG. 3 is a side, partially cut-away view of the backstop assembly, with the backstop wings 84 in their open, or deployed position;

FIG. 4 is a perspective view of the lower portion of the backstop assembly of FIG. 3, with the piston rod (94) in its intermediate position (i.e., piston lock pin 99 in upper channel 90);

FIG. 5 is a side plan view of the backstop wing members;

FIG. 7 is side view of a portion of housing 60 and the upper and lower portions of the backstop assembly, with the housing and tissue wall shown in cross-section, wherein the distal end of the backstop shaft has partially penetrated the tissue wall, with the wing members therefore compressed into the backstop shaft and the piston rod at its upper position (pin 99 above lower channel 91);

FIG. 8 is the same view of FIG. 7, however the wing members have now passed into the anatomical cavity, and are therefore deployed (i.e., open or expanded), with the piston rod now at its lower position (pin 99 in lower channel 91);

FIG. 9 is a cross-sectional view of FIG. 8, taken along the line 9—9 thereof;

FIG. 17 is a schematic side view of a portion of the body of the cutting blade assembly, with inner shaft 74 omitted for clarity, and with the thrust washer (150) positioned in the double-channeled slot (140);

FIG. 18 is a perspective view of a thrust washer according to one embodiment of the present invention;

FIG. 22 is a view of the lower portion of the apparatus shown in FIG. 21, wherein the cutting blades have contacted the wing members, and the cannula has been urged downwardly so as to extend through the entire depth of the tissue opening, thereby extending over the cutting blades and wing members;

FIG. 23 is the same view as FIG. 22, wherein the cutting blade assembly and the backstop assembly have been removed, leaving only the cannula in place within the tissue opening in order to provide surgical access to the anatomical cavity;

SUMMARY OF THE PREFERRED EMBODIMENTS

Figure 1:
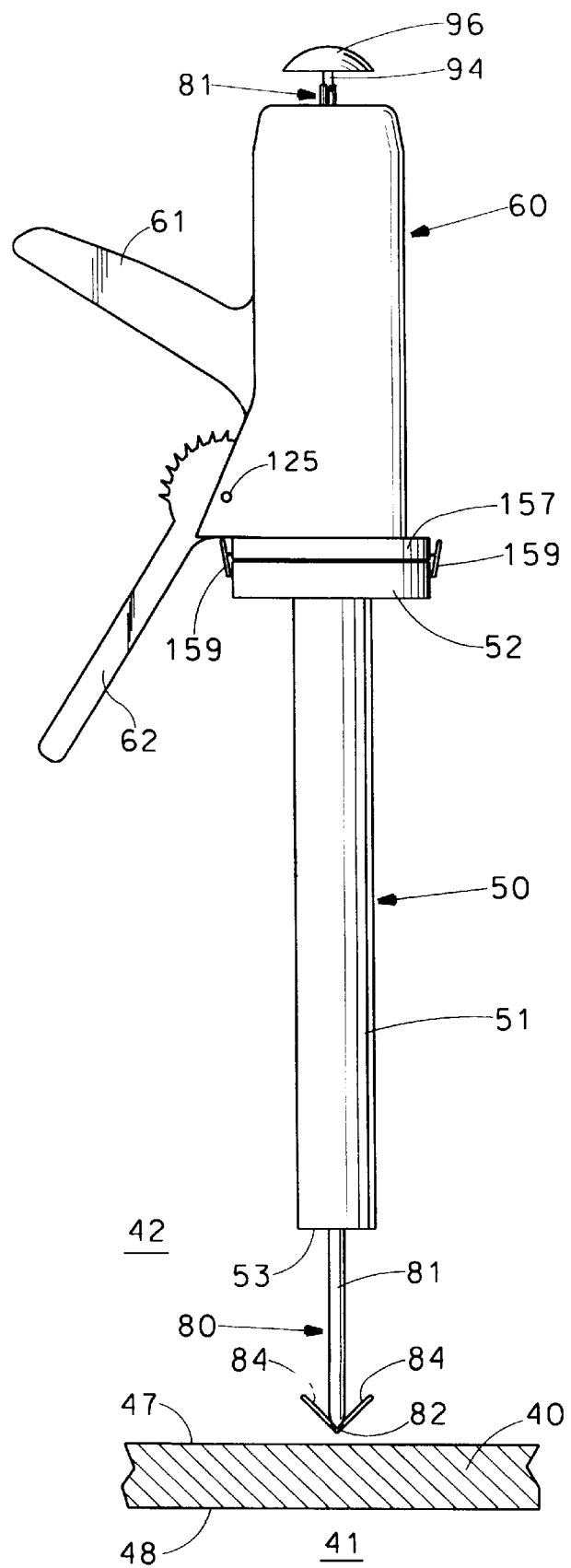
FIG. 1 is a side schematic view of a trocar according to the present invention, wherein a tissue wall 40 overlying an anatomical cavity 41 is also depicted.

It is an object of the present invention to provide apparatus and methods for penetrating tissue.

It is another object of the present invention to provide apparatus and methods for creating an opening in tissue wherein the opening provides access to an anatomical cavity.

It is yet another object of the present invention to provide a trocar which employs a backstop to prevent over-penetration of the cutting blade(s) (i.e., the obturator).

It is another object of the present invention to provide an instrument which may be used to direct and/or limit the penetration depth of a penetration member (such as the obturator of a trocar) through tissue.

Another object of the present invention is to provide apparatus and methods for the penetration of a tissue layer which include a backstop which is urged against one surface of the tissue layer in order to delineate the location of said surface, and therefore the thickness of the tissue layer.

It will be understood that while the present invention as a whole provides the foregoing objects, individual embodiments may not provide each and every one of the foregoing objects. Some of the foregoing objects may be provided, in accordance with one preferred embodiment of the present invention, by providing an instrument for the penetration of tissue, comprising:

(a) a backstop assembly having a shaft and a backstop; and (b) a penetration member slidingly engaged with the backstop shaft, and configured for penetrating tissue;

the backstop assembly and the penetration member configured such that the backstop may be positioned adjacent tissue to be penetrated, such that as the penetration member is urged through the tissue along the backstop shaft, the backstop will limit the depth of penetration of the penetration member through the tissue. The penetration member can essentially comprise any instrument which is urged through tissue, and it need not be an instrument which has a cutting blade or the like to allow for the cutting of the tissue upon penetration.

A trocar for penetrating the tissue wall of an anatomical cavity is also provided, and comprises:

(a) a cannula;

(b) a backstop assembly having a backstop, the backstop assembly positioned at least partially within the cannula; and (c) a cutting blade assembly slidably positioned at least partially within the cannula;

wherein the backstop may be urged through a tissue wall into an underlying anatomical cavity, and thereafter a distal end of the cutting blade assembly may be urged through the tissue wall towards the backstop. Preferably, the backstop is interposed between the cutting blade assembly and underlying anatomical structures which would be at risk without the use of a backstop.

An instrument for limiting the depth of insertion of a penetration member urged through tissue is also provided, the instrument comprising:

(a) a shaft; and (b) a backstop positioned at a distal end of the shaft;

wherein the backstop and the shaft configured such that the backstop may be positioned adjacent one side of the tissue to be penetrated, and a penetration member may thereafter be urged through the opposite side of the tissue into the backstop.

The present invention also provides a method of penetrating the tissue wall of an anatomical cavity, comprising the steps of:

(a) positioning a backstop within the anatomical cavity;

(b) urging a penetration member through the tissue wall of the cavity towards the backstop.

A method of penetrating the wall of an anatomical cavity is also included herein, and comprises the steps of:

(a) providing a backstop positioned at one end of a backstop shaft, and a penetration member;

(b) urging at least a portion of the backstop shaft through the wall such that the backstop is positioned within the anatomical cavity, the wall having exterior and interior surfaces;

(c) providing traction on the backstop shaft so that the backstop is urged against the interior surface of the wall, thereby delineating the location of the interior surface of the wall; and (d) urging the penetration member through the wall, while directing the depth of penetration by means of the backstop.

DETAILED DESCRIPTION OF THE INVENTION

The present invention provides apparatus and methods for penetrating tissue and creating an opening therein, particularly for creating tissue openings which provide access to anatomical cavities within a patient (both human and animal). More particularly, the apparatus and methods of the present invention create a tissue opening in which a cannula may be positioned, thereby providing a channel through which other instruments may be inserted (e.g., an endoscope) into the patient's body. When used in this manner, one embodiment of an apparatus according to the present invention is trocar, which includes the cannula as an integral part thereof. However, the present invention is by no means limited to trocars and methods employing trocars. In fact, the apparatus and methods of the present invention may be used to penetrate tissue and/or create tissue openings in a variety of medical procedures. Thus, although much of the present invention will be described in conjunction with the positioning of a cannula in a tissue opening to provide operative access to an anatomical cavity, particularly by means of a trocar having an integral cannula, it will be understood that the scope of the present invention is not so limited.

As used herein, the term "anatomical cavity" refers to any actual or potential space within the patient, including, for example, the abdominal cavity (both intra- and extraperitoneal), the thoracic cavity, organs, lumens, and even potential spaces (such as those often accessed during arthroscopic or laparascopic procedures; for example, the space of Retzius).

Unlike prior art trocars and other medical instruments used to penetrate or create openings in tissue, the apparatus and methods of the present invention utilize a backstop to prevent over-insertion of a penetration member (such as a cutting blade assembly). The backstop prevents the penetration member, particular the sharpened cutting element portion or blade of the penetration member, from advancing past a certain, predetermined location, thus preventing inadvertent injury to the patient. As used herein, the term "backstop" refers to any structural element which may limit or direct the depth of penetration of the penetration member, thereby preventing over-penetration. In a preferred embodiment, the backstop is first positioned within the patient's body, preferably adjacent to the tissue through which the cutting element will penetrate (e.g., within the anatomical cavity itself). The backstop is preferably aligned with the cutting element, or another structure associated therewith, such that once the cutting element has penetrated through the tissue the desired amount, the cutting element (or another structure associated therewith) will bear against the backstop, thereby preventing further advancement of the cutting element into the patient. An added benefit of a preferred embodiment is that the backstop will also act as a guard for the sharp edges of the cuffing element, thereby further preventing injury to the patient or medical practitioner as the cutting element is removed from the patient.

A preferred embodiment of an apparatus according to the present invention also has an integral cannula, as well as a housing which encloses certain mechanical structures of the device, and essentially comprises a trocar. Like prior art trocars, the cannula of the apparatus of the present invention may be released from the other structural components so that the cannula may remain in the tissue opening. The cannula is preferably sized and configured such that other medical instruments may be inserted therethrough, such as various types of endoscopes. The housing is preferably configured for ease of operation, and also preferably includes a handle and a deployment member for the controlled deployment of the penetration member.

The apparatus and methods of the present invention are particular suited for providing access to anatomical cavities, such as the abdominal cavity (intra- or extra-peritoneal). Thus, the apparatus of the present invention, as well as the methods of using the apparatus of the present invention, will be described in conjunction with the creation of a tissue opening which provides access to a patient's abdominal cavity and the positioning of a cannula therein. It will be understood, however, that the apparatus and methods of the present invention are not so limited.

In order to assist in the understanding of the more detailed description of preferred embodiments of the present invention which follow, a brief summary of the use of one preferred embodiment will now be described. The apparatus depicted in FIG. 1 essentially comprises a trocar assembly which includes a cannula 50. Cannula 50 may be configured similar to those provided on currently-available trocars, such as those described in U.S. Pat. Nos. 5,318,585, 5,342,382 and 5,366,445. Therefore, cannula 50 may optionally include various valves, ports and other features commonly found on cannulas used in surgical procedures in order to provide surgical access to an anatomical cavity. Cannula 50 is particularly suited for use in endoscopic procedures, and is therefore intended to be positioned within a tissue opening to provide access to an anatomical cavity through the interior of cannula 50.

At its upper end, the enlarged handle portion 52 of the cannula is releaseably attached to a housing 157 by means of cannula locks 159. Main housing 60 is located at an upper end of the trocar, and includes a handle 61 and blade advancement arm 62 which extend away from housing 60. Various mechanisms for activation and deployment of the components of the trocar depicted in FIG. 1 are contained within housing 60 and are described in greater detail below. It will be noted, however, that a backstop assembly is positioned at least partially within cannula sleeve 51, and a portion of the backstop assembly may extend away from the distal (or lower) end of cannula sleeve 51. This backstop assembly includes a backstop shaft 81 and a pair of backstop wings 84. It should be noted, however, that the backstop assembly may be positioned within the cannula such that no portion of the backstop assembly extends beyond the lower end of the cannula prior to activation and use of the device. A penetration member, or cutting blade assembly is housed within cannula sleeve 51 and main housing 60, and is therefore not visible in FIG. 1.

Figure 24:
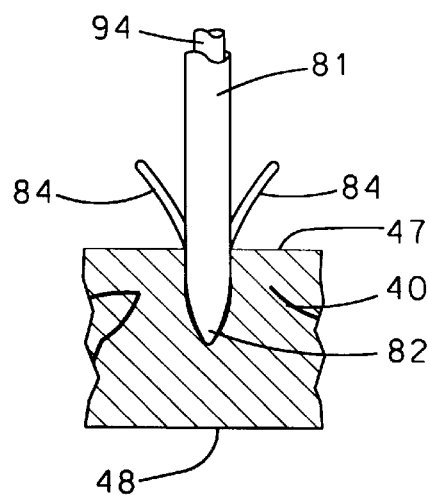
FIGS. 24–26 are sequential, schematic side views, depicting the passage of the backstop assembly through the tissue.
Figure 25:
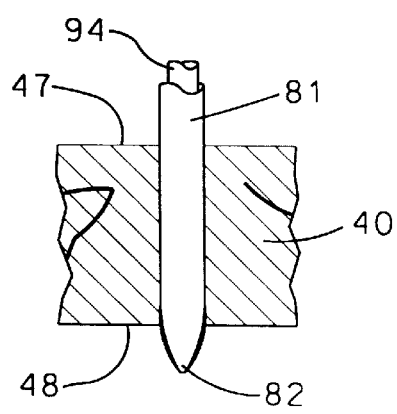
Figure 26:
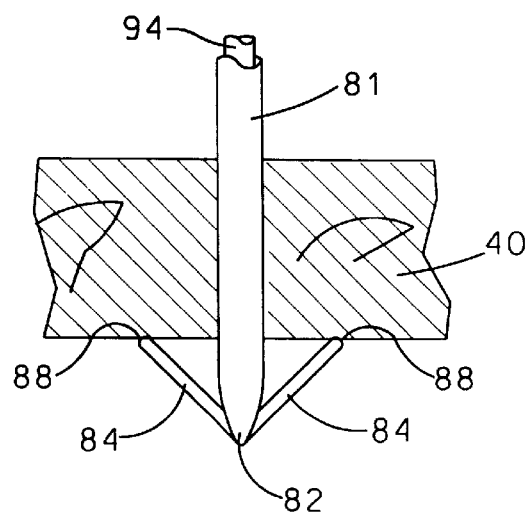

In order to use the apparatus in FIG. 1, the surgeon will prepare the patient in the typical manner for trocar insertion. Thus, depending upon the location of trocar penetration, the surgeon will insufflate the anatomical cavity to be accessed (particularly if it is the abdominal cavity), and a small incision (about 1 to about 2 mm in length) is made at the selected location of trocar insertion. In most cases, this incision need only penetrate the patient's skin. Next, lower (or distal) end 82 of backstop shaft 81 is urged through the incision in the direction of the anatomical cavity to be accessed. Distal end 82 need not be sharp, since the small gage of shaft 81 (about 1 to about 3 mm in diameter) will allow its distal end 82 to easily penetrate through most tissue layers (including the peritoneum). As backstop shaft 81 is continued to be urged through the tissue to be penetrated, wings 84 will be compressed to a position adjacent (i.e., next to or against), or even into, shaft 81 (as seen in FIGS. 24 and 25). As wings 84 are compressed towards or into shaft 81, piston rod 94 (visible at the upper end of housing 60 in FIG. 1) along with its end cap 96 will move upwardly (FIG. 7). Once backstop wing members 84 have completely penetrated through the tissue layer into the anatomical cavity, wings 84 will return to their deployed, or open position, thereby preventing backstop shaft 81 from being removed from the anatomical cavity (as seen in FIG. 26). The deployed or open wings essentially increase the diameter of the lower end of backstop shaft 81 beyond the diameter of the small tissue opening created by the passage of the backstop shaft through tissue 40. In addition, as backstop wings 84 redeploy, piston rod 94 will move downwardly (preferably under the influence of a compression spring), and its end cap 96 will strike the upper end of shaft 81, producing visible and audible indicia of that the backstop is now located in the anatomical cavity.

Backstop wing deployment (FIG. 26) also causes the cutting blade assembly (i.e., the penetration member) to be released or activated within main housing 60. Prior to its release, the cutting blade assembly is locked in place and cannot be advanced towards the tissue to be penetrated or the backstop. Once released, however, the surgeon may advance the cutting blade assembly towards the tissue and backstop, such as by squeezing blade advancement arm 62 towards handle 61.

Figure 15:
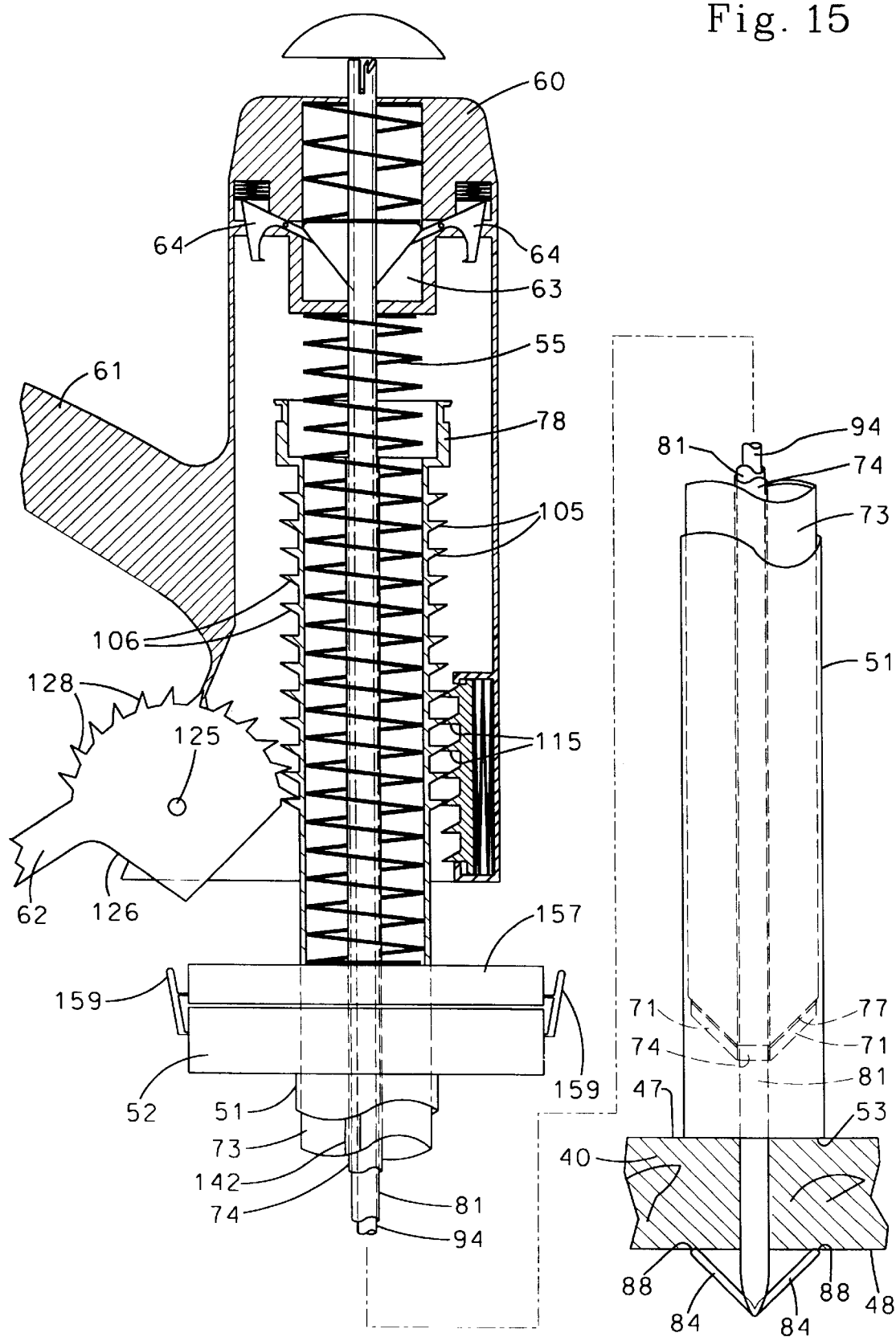
FIG. 15 is the same view as FIG. 2, however the backstop is positioned within the anatomical cavity, the cutting blade assembly and cannula have been released, and the cutting blade assembly advanced slightly towards the backstop.

Release of the cutting blade assembly within housing 60 also causes housing 157 to be released from its initial position adjacent the lower end of housing 60 (see FIG. 1). Since housing 157 is spring-biased downwardly, its release will force housing 157, as well as cannula 50 attached thereto, in the downward direction, such that the distal end surface 53 of the cannula will be urged against outer surface 47 of tissue 40 (as shown in FIG. 15). The spring-biasing of housing 157 and cannula 50 essentially forces main housing 60 and lower housing 157 away from one another. Since backstop shaft 81 is rigidly secured within housing 60, this downward spring-biasing of lower housing 157 and cannula 50 will likewise result in a similar upward (or traction) force on the backstop assembly (including backstop wings 84). In this manner, backstop wings 84 will be urged against inner surface 48 of tissue 40, and will therefore delineate the location of inner surface 48, and over-penetration of the backstop shaft will also be prevented. In addition, and as best seen in FIG. 15, tissue 40 will be compressed between distal end surface 53 of cannula 50 and backstop wings 84, thereby retaining (and stabilizing) distal end surface 53 of cannnula 50 against outer surface 47 of tissue 40. In fact, the surgeon may even pull upwardly on housing 60 in order to further tent up tissue 40, further moving the penetration site away from any underlying structures which should be avoided.

Main housing 60 also includes an anti-reversing mechanism which prevents the cutting blade assembly from moving in the upward direction. In this manner, the apparatus of the present invention cannot be "rearmed" once the cutting blade assembly has been released within housing 60, particularly after the cutting blade advancement has been advanced towards backstop wings 84 by means of arm 62. As blade advancement arm 62 is urged towards handle 61, the cutting blade assembly will be urged further downwardly such that a pair of cutting blades 71 on the cutting blade assembly will begin to penetrate tissue 40. In addition, the cutting blade assembly also preferably includes an inner shaft through which backstop shaft 81 is slidingly inserted. In this manner, the cutting blade assembly will slide downwardly along backstop shaft 81 towards wings 84. Each cutting blade 71 is also aligned with a corresponding backstop wing 84. Of course it is also contemplated that the shaft of the cutting blade assembly can be positioned within the backstop shaft, with the cutting blade(s) extending through suitable elongate slots extending through the wall of the backstop shaft.

Figure 21:
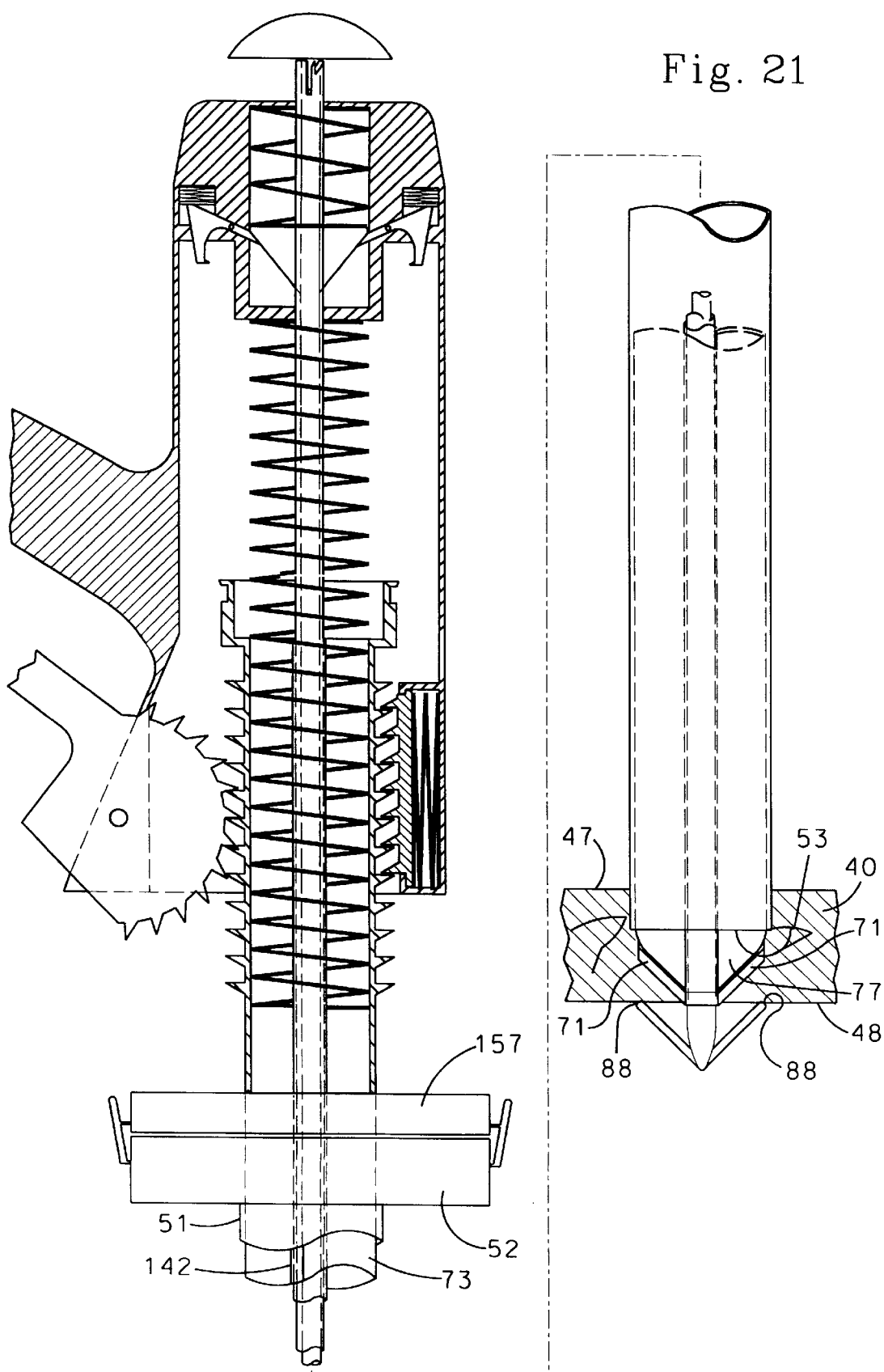
FIG. 21 is the same view as FIG. 16, however the cutting blade assembly has been further advanced downwardly through the tissue wall, with the lower end of the cannula following close behind and extending through a portion of the tissue opening.

As the cutting blade assembly is urged further downwardly (FIG. 16), the cannula itself will initially not move further downwardly, since movement is prevented by the contact between distal end surface 53 of the cannula and outer surface 47 of the tissue being penetrated. The cutting blade assembly, however, has a tapered lower end 77 adjacent to cutting blade 71, such that as blades 71 are urged through the tissue, tapered distal end 77 will expand the tissue opening created by the cutting blades. As the cutting blades are continued to be urged downwardly through the tissue, the tissue opening will progressively expand as tapered lower end 77 of the cutting blade assembly also passes through the tissue. Since cannula 50 is spring-biased in a downward direction, the expansion of the tissue opening will allow the lower end of the cannula to be forced therethrough. Therefore, as the cutting blades continue to penetrate the tissue wall, the lower end of cannula 50 will follow closely behind the cutting blades (FIG. 21).

As the cutting blade assembly is continued to be urged downwardly through the tissue by means of advancement arm 62, cutting blades 71 will eventually contact backstop wings 84. At this point, further advancement of the cutting blade assembly will not be possible. However, since cannula 50 may move independently of the cutting blade assembly, the downward force asserted by the spring-biasing on the cannula will cause the cannula to be urged completely through the tissue opening, and past the cutting blades and backstop wings which are now in contact with each other (FIG. 22). At this point, cannula locks 159 may be deactivated so as to release handle 152 of cannula 50 from housing 157. The surgeon may then pull upwardly on main housing 60, and thereby extract the backstop and cutting blade assemblies from cannula 50. The result is that cannula 50 extends through the tissue opening thus created into the anatomical cavity (FIG. 23). During the above-described process, the backstop prevents over-penetration of the cutting blades by not only limiting the depth of penetration of the cutting blade assembly, but also by providing an upward traction on the tissue being penetrated. Therefore, this apparatus provides for reduced risk of patient injury during cannula insertion.

FIG. 1 is a side view of one embodiment of an apparatus according to the present invention, wherein a portion of a patient's tissue 40 is also shown in cross-section. For purposes of description, tissue 40 may comprise a tissue wall (such as the abdominal wall) which overlies an anatomical cavity 41 (such as the abdominal cavity). The apparatus and methods of the present invention can be used to create an opening in tissue 40 which provides access from the exterior (or ambient) 42, to the interior of cavity 41. Tissue 40 will generally comprise a layer of skin, an underlying fat layer (of varying thickness), fascia, muscle, and, depending upon the location of the abdominal cavity being accessed, possibly the peritoneum. While the tissue to be penetrated by the apparatus of the present invention will, in most instances, include most of these layers, it will be understood that some tissue regions whereat the apparatus and methods of the present invention may prove useful will not have one or more of these specific layers (especially the peritoneum). Thus, the present invention is not considered limited to only the penetration of tissue regions having each and every one of the above-described tissue layers, as it may be used to penetrate a variety of tissue walls.

With prior art trocars, the cutting tip (or blade) of the obturator is simply driven through tissue 40 until the cutting tip passes into abdominal cavity 41. Unless an endoscope has been previously inserted through another tissue opening, the medical practitioner must rely upon his own experience to gauge the depth of penetration. Even when visualization of the interior of the cavity being penetrated is provided (such as through a laparoscope), proper insertion depth may be difficult to achieve. If penetration is too deep, particularly if the insertion angle of the trocar is incorrect, the cutting tip may inadvertently pierce one or more organs or blood vessels in the abdominal cavity. This damage can be fatal, particularly if a major blood vessel such as the aorta is unknowingly pierced. Insufflation of the abdominal cavity can reduce the possibility of trocar injury, since the insufflation essentially increases the distance between tissue 40 and the structures therebeneath which must be avoided. The additional air space also assists the surgeon in detecting when the cutting tip has penetrated the abdominal cavity. The surgeon may also manually tent up tissue 40, such as by physically grasping and pulling upwardly on a portion of tissue 40, thereby further distancing tissue 40 from the underlying structures which must be avoided. While the commonly-available safety trocars may reduce the chance of injury, particularly when used with insufflation and manual tenting-up of tissue 40, the number of trocar injuries and deaths is nevertheless alarming and on the rise.

Figure 2:
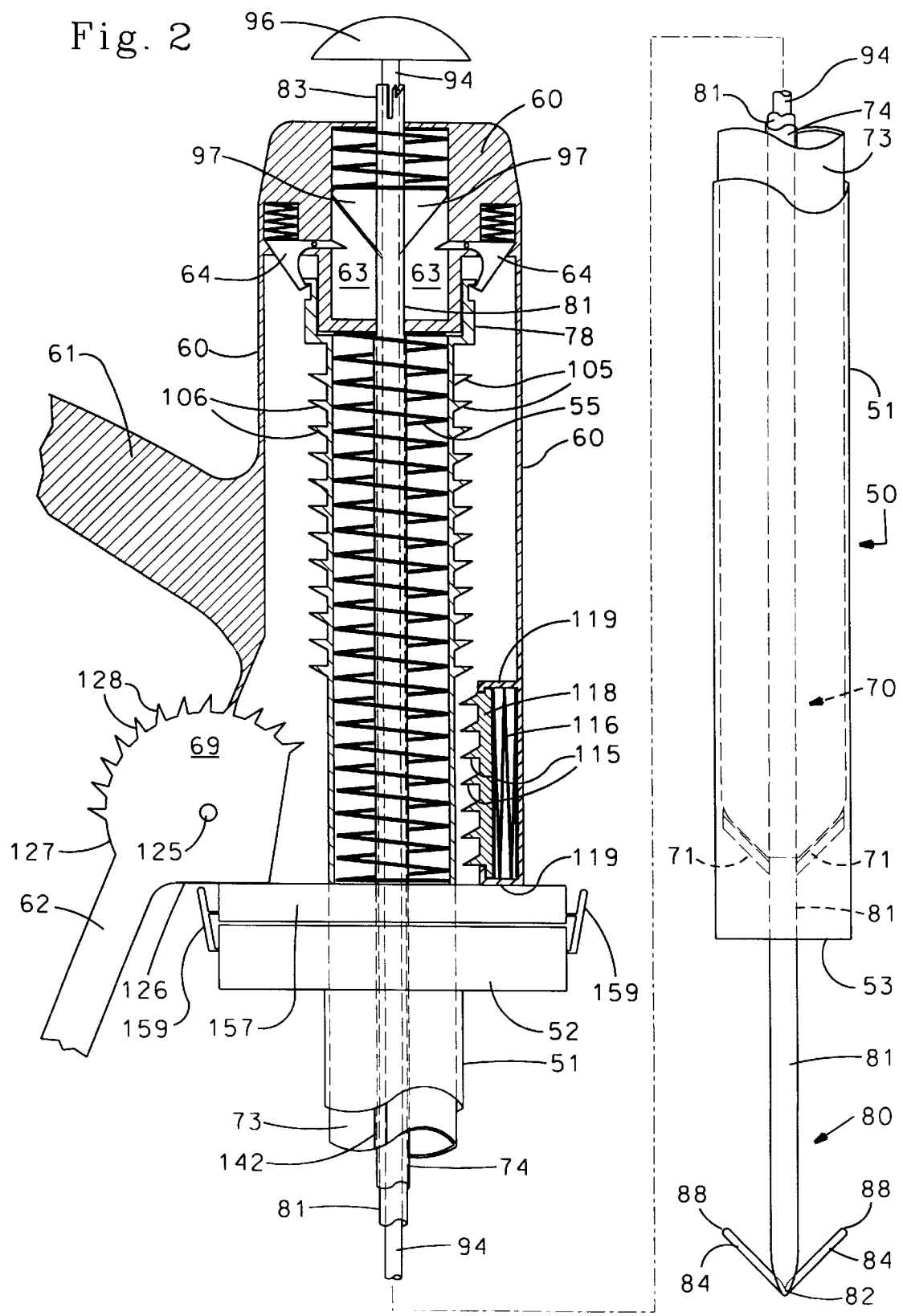
FIG. 2, is a partially cut-away view of the apparatus of FIG. 1, shown in its initial, or unactivated state (backstop wings deployed, cutting blade assembly and cannula retained within housing)

As best seen in FIGS. 1 and 2, one embodiment of the apparatus of the present invention generally comprises a cannula 50, a housing 60, a penetration member (or cutting blade assembly) 70, and a backstop assembly 80. The apparatus of the present invention shown in FIGS. 1 and 2 may be employed to penetrate the tissue wall of an anatomical cavity, thereby creating an opening in the tissue wall within which cannula 50 may be inserted. Cannula 50 may be similar to those found on currently-available trocars, and may include any of the features found on such cannulas (e.g., a flapper valve which prevents the escape of insufflation gas).

As more fully described herein, tissue penetration may be accomplished, for example, by passing lower (or distal) end 82 of backstop assembly 80 through the tissue to be penetrated. Thereafter, cutting blade assembly 70 is advanced towards lower end 82 of backstop assembly 80 such that cutting blade assembly 70 will be urged through the tissue, thereby creating an opening therein. Over penetration of cutting blade assembly 70 is prevented by backstop assembly 80. Cannula 50 may either follow through the tissue along with cutting blade assembly 70, or it may be urged through the tissue after the cutting blade assembly has created the opening therein. Thereafter, backstop assembly 80 and cutting blade assembly 70 are preferably removed and discarded, such that cannula 50 will remain in place. Although backstop assembly 80 and cutting blade assembly 70 may be advanced through the tissue by any of a variety of means, one preferred embodiment also employs actuating and advancement mechanisms contained within housing 60 for the controlled advancement of cutting blade assembly 70.

FIG. 3 is a partially cut-away, side view of one embodiment of backstop assembly 80 according to the present invention. In the embodiment shown, the backstop itself is provided by a pair of flexible wings 84 which extend away from an elongate, hollow backstop shaft 81, adjacent distal end 82. Backstop shaft 81 may be of spherical cross-sectional shape, however a non-spherical shape (such as elliptical) may also be employed in order to allow shaft 41 to be non-rotatingly positioned within the inner shaft of the cutting blade assembly (as further described below). Distal end 82 is preferably blunt in order to prevent inadvertent injury to the patient or surgeon, however it can be sharp if desired. Distal end 82 may be inserted through a small stab incision in the tissue to be penetrated, and thereafter urged through any layers of fat, muscle, fascia, and other tissue layers present (including the peritoneum). Because of the small gauge of the backstop shaft (about 1 to about 3 mm in diameter), distal end 82 can be easily urged through such tissue layers, even the peritoneum.

As mentioned above, the backstop feature of the apparatus of the present invention may comprise a pair of flexible wings 84 which extend away from opposite sides of backstop shaft 81 adjacent (i.e., at or near) its distal end 82. Wings 84 are movable between open (or expanded) and closed (or compressed) positions, and may comprise any structure which may be moved between such positions. Therefore, the cylindrical wire shape depicted is merely one preferred embodiment. For example, wings 84 can comprise flat plates which may be retracted into shaft 81 for closure, and even members contained within shaft 81 which may be urged outwardly through suitable openings in shaft 81 to an open (or deployed) position. Thus, the term "wings" refers to any of a variety of structural members which may be moved between a retracted (or closed) position, and an expanded (or open) position which provides a larger diameter for the backstop assembly at the lower end from which the wings extend when in their open position. In this manner, distal end 82 of backstop shaft 81 may be urged through tissue with the wings in their closed (or retracted) position, and, once the wings are in the anatomical cavity and have redeployed (or expanded), removal of the wings and shaft 81 from the cavity is not possible.

In the embodiment shown, wings 84 are in their open, or deployed, position in FIG. 3, wherein wings 84 extend angularly away from backstop shaft 81. Since shaft 81 may be made from, for example, metal or plastic, wings 84 may be molded integrally with shaft 81 in the open position depicted in FIGS. 3 and 4. Alternatively, wings 84 may be manufactured separate and apart from shaft 81, and thereafter secured to shaft 81 in the appropriate position. Each wing 84 may be manufactured as a separate element, or, as shown in FIG. 5, a pair of wings 84 may be manufactured as a single, integral structure. In the embodiment of FIG. 5, wings 84 comprise a pair of elongate, preferably cylindrical members which are connected to one another in a V-shaped configuration. An aperture 85 may be provided in the region where wings 84 meet in order to simplify the attachment of wings 84 to the backstop assembly. A pin, or other suitable fastener (not shown), may extend through aperture 85 and be secured within distal end 82 of shaft 81, thereby securing wings 84 to shaft 81. When wings 84 are manufactured as separate and distinct components, they may be secured to shaft 81 in a similar manner.

Figure 11:
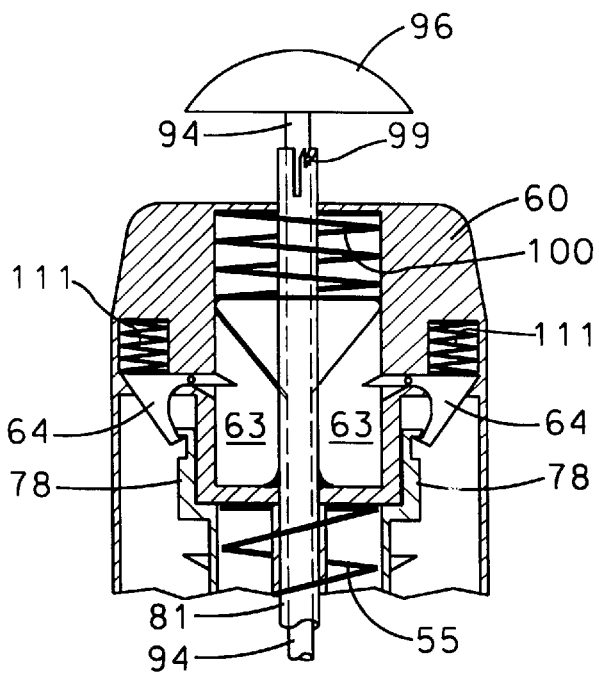
FIG. 11 is side view of an upper portion of the apparatus of FIG. 2, with the housing and cutting blade assembly shown in cross-section.

As yet another alternative, wings 84 may be secured to shaft 81 by the various manners shown and described in U.S. Pat. Nos. 5,417,712 and 5,522,845 for attaching the "bone-engaging means" or "barbs", as those terms are used in these two patents, to the anchors described therein. For example, in a manner similar to that shown in FIG. 11 of U.S. Pat. No. 5,522,845, a pair of cylindrical bores may be provided in distal end 82 of shaft 81, and a pair of cylindrical wings 84 may be secured within such bores (e.g., similar to the manner in which barbs 20 are secured within bores 70 in the anchor device shown in FIGS. 4 and 11 of the '845 patent).

As mentioned previously, wings 84 may also take any of a variety of shapes, and the cylindrical configuration depicted is merely one preferred embodiment. As will be more fully described herein, wings 84 should have a sufficient length and surface area to ensure that they will act as a backstop for the cutting blades. Therefore, the length, and even the shape of wings 84 will depend, in part, upon the size and configuration of the cutting elements used in the apparatus. Although the cylindrical shape is preferred, particularly because of ease of fabrication and reduced potential for patient injury, wings 84 may comprise elongate members having a rectangular, elliptical, triangular, or any other of a variety of cross-sectional shapes.

As mentioned above, wings 84 are depicted in FIGS. 3–5 in their open, or deployed state. In this position, wings 84 are generally in a V-shaped configuration whereby each wing 84 extends angularly away from shaft 81. Wings 84, however, should also be inwardly closable, such that wings 84 may be urged towards shaft 81 as indicated by the arrows in FIG. 4. In other words, wings 84 are moveable between the deployed state shown in FIG. 4, and the undeployed, or closed configuration depicted in FIG. 7. Each wing 84 may, for example, pivot or flex towards shaft 81 such that the distance between each of the wing members is decreased. Preferably, wings 84 pivot or flex to a position wherein each wing lies at least adjacent to the external surface of shaft 81. More preferably, a pair of longitudinal wing slots 87 are provided on opposite sides of shaft 81, and extend from distal end 82 towards proximal end 83 of shaft 81. Since shaft 81 is preferably hollow, longitudinal wing slots 87 may be sufficiently deep so as to extend the full thickness of the wall of shaft 81, thereby providing communication between the interior of shaft 81 and its exterior. In addition, wings 84 are preferably attached to shaft 81 such that each wing extends out of the interior of shaft 81 through that portion of a corresponding wing slot 87 which is nearest distal tip 82 of shaft 81, as best shown in FIG. 4.

Each longitudinal wing slot 87 further preferably extends parallel to the longitudinal axis of shaft 81, as well as parallel to one of wings 84. In addition, wing slots 87 are preferably sized such as that as wings 84 flex or pivot inwardly (in the direction of the arrows shown in FIG. 4), wings 84 will be received within slots 87 (as best shown in FIG. 7). In this manner, when wings 84 move from their open (or deployed) position to their closed (or undeployed) position, little or no portion of each wing 84 will extend beyond the exterior surface of shaft 81.

Wings 84 may pivot or flex into wing slots 87 in a variety of manners. For example, when each wing 84 is provided as a separate structure, each wing may independently pivot about an axis located, for example, in the same location as aperture 85 in FIG. 5. Preferably, wings 84 are manufactured from a flexible or elastic material which can be resiliently flexed from the open to the closed position. For example, if the wing assembly of FIG. 5 is made from any of a variety of plastics, it will be apparent that wings 84 will be capable of flexing inwardly towards one another due to the inherent resilient nature of many plastics. Similarly, and as presently preferred, wings 84 are made from a shape memory alloy such as nitinol. Such materials are elastic (or pseudoelastic) in nature, yet will return to their original shape when the flex-inducing force is removed. In addition, such alloys are also generally stronger than most plastics, and are therefore less likely to break upon flexing. It should be noted that all of the various components of the present invention may be made from a variety of medically-approved materials, including various metals (particularly stainless steel) and plastics. Metal is preferred for the cutting blades (particularly stainless steel), and the various springs described herein.

The specific material used for manufacturing wings 84, as well as the overall configuration of the wing assembly itself (such as the assembly depicted in FIG. 5) should be selected such that a force supplied to wings 84 in the direction of the arrows shown in FIG. 4 will cause the desired inward flexing of wings 84 (to the position shown in FIG. 7). When this force is released, however, wings 84 should immediately return to their open or undeployed state (FIG. 4). While shape memory alloys and many plastics can inherently provide this feature, it is also contemplated that a spring or other suitable mechanism may also be employed for this purpose, particularly when wings 84 are designed such that closure is the result of wing pivot rather than wing flex. As more fully described below, however, the materials and overall configuration of the wing assembly should also be chosen such that sufficient force to fully close wings 84 can be provided by the patient's tissue as the distal end region of shaft 81 (including the wing assembly) is urged through the patient's tissue.

FIGS. 24–26 depict, in sequence, the manner in which the backstop is passed through the outer or first surface 47 of tissue 40 towards the interior or second surface 48. Since distal end 82 of shaft 81 is preferably blunt, it will often be necessary to first create a small incision (about 1 to about 2 mm in length) in outer surface 47. This is particularly true when outer surface 47 comprises the patient's skin, such as when the apparatus of the present invention is used as a trocar. The incision, however, need only penetrate the layer of skin, since blunt end 82 will be capable of passing through the tissue layers therebeneath (such as the fascia, muscle, and even the peritoneum).

Once the incision has been made at the tissue penetration site, end 82 of shaft 81 is urged therethrough, as seen in FIG. 24. As shaft 81 passes through tissue 40, the various layers of tissue 40 will act to compress wings 84 inwardly, as shown. As shaft 81 penetrates tissue 40 even further, as shown in FIG. 25 wings 84 will be fully compressed into longitudinal wing slots 87, and will therefore not hinder passage of shaft 81 through tissue 40. Once shaft 81 has been sufficiently urged through tissue 40 such that tips 88 of wings 84 have passed beyond the interior surface 48 of tissue layer 40, the tissue will no longer apply a compressive force against any portion of wings 84. Thus, wings 84 will return to their original, deployed (or expanded) state, as seen in FIG. 26.

As also seen in FIG. 26, tips 88 of wings 84 will prevent withdrawal of shaft 81 once shaft 81 has penetrated tissue 40 into the anatomical cavity and wings 84 have redeployed. In addition, upward traction on shaft 81 will urge tips 88 against interior surface 48 of the tissue, thereby delineating the precise location of surface 48. Graduations or other indicia may also be provided on shaft 81 in order to provide an indication of the thickness of tissue layer 40. In this manner, the backstop assembly may also direct passage of the penetration member by the mere fact that the surgeon will now know exactly how deep the penetration member must travel through tissue layer 40 in order to reach the underlying anatomical cavity. The thickness of tissue layer 40 can also be used to ensure that a properly sized penetration member is used. Furthermore, upward traction on the backstop assembly also helps to tent-up the tissue wall, thereby further moving tissue wall 40 away from any underlying structures which must be avoided.

As mentioned previously, shaft 81 is preferably hollow, thereby accommodating a piston rod 94 therein. In a preferred embodiment, piston rod 94 serves two purposes, namely providing a visual and/or audible verification of wing deployment, and providing a mechanism by which deployment of wings 84 causes the release (or activation) of the cutting blade assembly. Thus, piston rod 94 is slidable within the interior of shaft 81, and is also responsive to the closing and opening of wings 84. As best seen in FIG. 4, the distal end portion 95 of piston rod 94 is tapered, and piston rod 94 is initially positioned such that its tapered distal end 95 is spaced away from distal tip 82 of shaft 81. Tapered distal end 95 should, however, be initially positioned such that it is visible and accessible through longitudinal wing slots 87 in shaft 81 (i.e., it underlies a portion of wing slots 87). Since the wall thickness of shaft 81 at wing slots 87 is preferably less than the diameter of wings 84, as wings 84 are urged into wing slots 87 they will impart a compressive force against tapered distal end 95 of piston rod 94. This compressive force on tapered end 95 will urge piston rod 94 in the direction of the arrow shown in FIG. 4 on piston rod 94, as also shown in the lower half of FIG. 7. In this manner, the closing (or undeployment) of wings 84 urges piston rod 94 upwardly away from distal end 82 of shaft 81.

Figure 6:
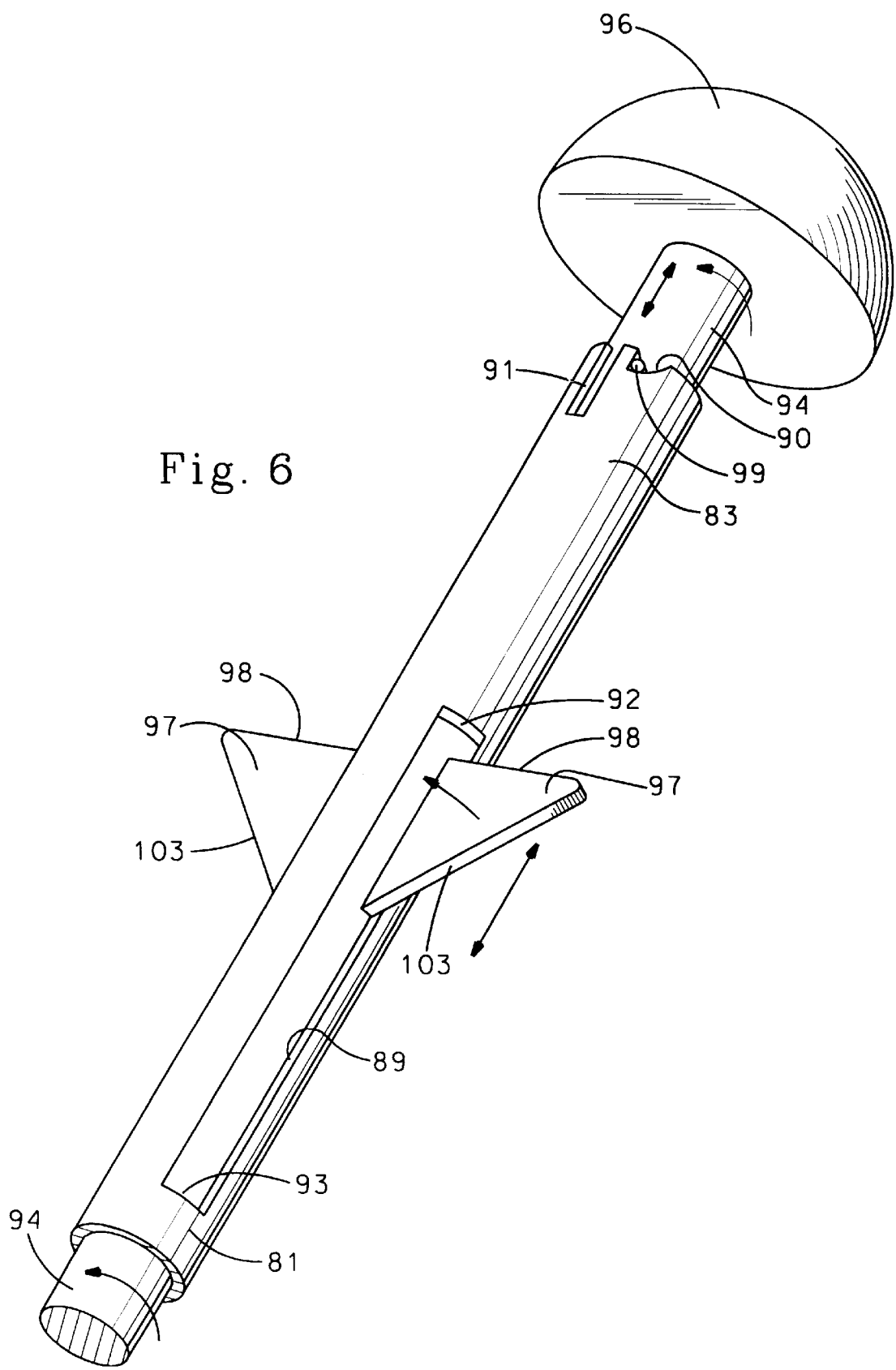
FIG. 6 is a perspective view of the upper portion of the backstop assembly, with the wing members and piston rod in the same position as in FIG. 4.

As best seen in FIG. 6, the proximal end of piston rod 94 preferably has an end cap 96 secured thereto. Proximal end cap 96 may be attached to piston rod 94 by any of a variety of means, such as providing male threads on the end of piston rod 94 and corresponding female threads on end cap 96. Although proximal end cap 96 is depicted as being hemispherical in shape, any of a variety of shapes may be employed. Preferably, proximal end cap 96 has a diameter which is greater than that of proximal end 83 of shaft 81.

Piston rod 94 also has a lock pin 99 which extends radially outward from the exterior surface of rod 94. Lock pin 99 is preferably positioned adjacent to, but spaced away from end cap 96 (as shown in FIG. 6), and is positioned so as to be nestible within an upper, or first, channel 90 provided at proximal end 83 of shaft 81. Upper channel 90 in shaft 81 may be any of a variety of shapes, however, it should be configured such that it will retain lock pin 99 therein, thereby preventing piston rod 94 from inadvertently advancing towards wings 84. In fact, when piston rod 94 is in its initial position shown in FIG. 4, lock pin 99 will be held within channel 90.

As wings 84 are compressed into wing slots 87, thereby urging piston rod 94 upwardly (i.e., away from distal end 82 of shaft 81), lock pin 99 will move upwardly away from first channel 90. Piston rod 94, however, is also preferably spring-biased in a clockwise direction, such that when piston rod 94 is urged upwardly by the closure of wings 84 and lock pin 99 therefore moves out of first channel 90, piston rod 94 will rotate in a clockwise manner within shaft 81. Thus, first channel 90 should also be configured so as to prevent premature rotation of piston rod 94 while lock pin 99 remains in first channel 90.

A preferred embodiment of the present invention also includes a mechanism for limiting the movement of piston rod 94, both longitudinally and rotationally, within backstop shaft 81. Therefore, as best seen in FIG. 6, piston rod 94 has a pair of release arms 97 which extend radially away from opposite sides of piston rod 94. A pair of slots 89 are provided in shaft 81, and release arms 97 extend therethrough. When the backstop assembly of the present invention is in its initial position wherein lock pin 99 is located within first channel 90 of shaft 81, release arms 97 will be positioned as shown. Slots 89 in shaft 81 should be sized and positioned such that piston rod 94 and its release arms 97 may move upwardly a sufficient amount to enable lock pin 99 to be released from first channel 90. Upper edge 92 of slots 89, however, should be positioned so as to limit the upward movement of piston rod 94, including preventing its removal from shaft 81, without interfering with the release of lock pin 99 from upper or first channel 90. Slots 89 should also have a width which limits the clockwise rotation of piston rod 94.

Shaft 81 also has a second, or lower channel 91 at proximal end 83, wherein second channel 91 is adjacent to, and longer than first channel 90. The purpose of second channel 91 is best seen in the sequence depicted in FIGS. 7 and 8. In FIG. 7, wings 84 have been compressed as the distal tip of shaft 81 is urged through tissue 40. Compression of wings 84 has in turn caused piston rod 94 to move upwardly, thereby releasing lock pin 99 from first channel 90. Since piston rod 94 is spring-biased clockwise, once lock pin 99 is released from first channel 90, piston rod 94 rotates clockwise until lock pin 99 is aligned with second channel 91. Over-rotation of piston rod 94 is prevented by proper sizing of the width of slots 89 in shaft 81 through which release arms 97 extend. Once shaft 81 has penetrated tissue 40 sufficiently such that wings 84 are released (as seen in FIG. 8), wings 84 will no longer apply a compressive force to the tapered distal end 95 of piston rod 94. Since piston rod 94 is also spring-biased downwardly, redeployment of wings 84 will allow piston rod 94 to be urged downwardly by the spring-biasing, with lock pin 99 passing into second, or lower channel 91. Since second channel 91 is longer than first channel 90, tapered distal end 95 of rod 94 will also drop down further than its initial position of FIG. 4 as shown in the lower half of FIG. 8. In this manner, if further upward movement of piston rod 94 is prevented, tapered distal end 95 of rod 94 will assist in preventing closure of wings 84, thereby assisting in preventing withdrawal of the backstop assembly from the patient's tissue. Although various locking mechanisms may be employed for preventing upward movement of piston rod 94 after it has reached its deployed position shown in FIG. 8 including the downward spring-biasing of piston rod 94, upward movement may also be prevented merely by the surgeon applying downward force on proximal end cap 96 of rod 94.

As mentioned above, piston rod 94 is preferably spring-biased in a clockwise direction. Various spring mechanisms, or other types of mechanical rotators, may be employed for this purpose. In a preferred embodiment, however, a helical spring which acts upon release arms 97 is employed to spring-bias piston rod 94 in the desired direction. Since helical springs respond to both torsional and translational forces, this helical spring may also be used to spring-bias piston rod 94 in the desired downward direction (i.e., towards distal end 82 of shaft 81).

As seen in FIGS. 2 and 7, housing 60 has a release chamber 63, which is preferably cylindrical and centered within the upper end of housing 60. Backstop shaft 81 extends through the center of release chamber 63, and is preferably secured therein such as by adhesive or other suitable means. In this manner, movement of backstop shaft 81 with respect to housing 60 is prevented. Shaft 81 is also positioned such that release arms 97 of piston rod 94 are positioned within release chamber 63 of housing 60 as shown. Helical spring 100 is positioned between the upper edge 98 of each release arms 97 and the upper wall of release chamber 63. Thus, when properly loaded, helical spring 100 can cause movement of release arms 97, and in turn, piston rod 94 to which they are attached, with respect to the upper wall of release chamber 63.

Figure 27:
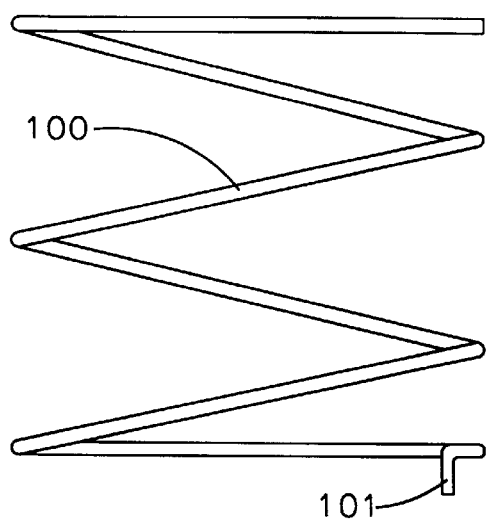
FIG. 27 is a side view of the helical spring used for spring-biasing of the piston rod.

Helical spring 100 is preferably loaded such that release arms 97 are spring-biased in both the downward and clockwise directions. The downward force is provided due to the spring being compressed between the upper wall of release chamber 63 and upper edge 98 of release arms 97. Rotational force is provided by helical spring 100 acting on at least one of release arms 97. As seen in FIG. 27, the lower most revolution of helical spring 100 includes a downwardly-extending tail portion 101. As best seen in FIG. 9, tail portion 101 of spring 100 is positioned against the surface of right release arms 97. Before being positioned in this manner, helical spring 100 is loaded counter-clockwise, thereby spring biasing right release arms 97 clockwise. In turn, piston rod 94 will therefore also be biased in a clockwise direction. It may also be necessary to secure the spring 100 to the upper wall of chamber 63 such as by use of adhesive or even by means of an upwardly-extending tail on spring 100 which is secured to or within the upper wall of chamber 63.

The downward force provided by helical spring 100 will also assist in deploying wings 84 once the wings have passed completely through tissue 40. Once piston rod 94 has been urged upwardly by wings 84, thereby releasing lock pin 99 from first channel 90, piston rod 94 will rotate clockwise thereby positioning lock pin 99 directly above second channel 91 in shaft 81. Helical spring 100 with thereafter provide a downward force on piston rod 94, thereby helping to redeploy wings 84 once they have passed completely through tissue 40. In addition, this forcible downward movement of piston rod 94 will also cause proximal end cap 96 to strike proximal end surface of shaft 81, thereby providing both visual and audible indications of backstop deployment. In this manner, the surgeon will be certain that wings 84 have been deployed within the anatomical cavity being penetrated, with tips 88 of wings 84 positioned against inner surface 48 of tissue 40. This visual and audible indication of proper wing deployment will also help prevent over-insertion of backstop shaft 81, thereby assisting in preventing inadvertent injury to the patient.

The backstop assembly and penetration member (i.e., the cutting blade assembly) are configured such that once the backstop is positioned within the anatomical cavity adjacent to the interior surface of the tissue wall, the backstop and penetration member may be advanced towards one another. The phrase "advanced towards one another," as used herein, simply means that the penetration member is advanced towards the backstop, the backstop is advanced towards the penetration member, or the penetration and backstop are simultaneously advanced towards each other. In other words, in a preferred embodiment, the cutting blades of the penetration member are urged through the tissue towards the backstop, and/or the backstop is pulled towards the cutting blade. Regardless, the result is that the penetration member will be urged through the tissue wall, with the backstop limiting the depth of penetration. Preferably, the backstop acts on the penetration member by direct contact with the cutting (or blade) portion of the penetration member. Of course, it is also contemplated that the backstop may limit the depth of penetration by directly contacting other portions of the penetration member (or even other structures associated with the penetration member) in order to prevent further advancement of the penetration member (including the cutting elements) through the tissue.

Turning to FIG. 15, wherein wings 84 have been advanced through tissue 40 and are shown fully deployed against inner surface 48 of tissue 40, the penetration member, i.e., cutting blade assembly 70, has a pair of cutting blades 71 at its lowermost end. It will be understood, however, that the cutting element(s) employed may vary considerably, and the flat blades shown are merely a currently-preferred embodiment. Cutting elements having pointed tips, flattened blade portions, and the like are all within the scope of the term "cutting blade" used herein. And one or more cutting blades may be used, however it is preferred that the number of cutting blades correspond to the number of backstop members. As more fully described below, cutting blade assembly 70 is also preferably slidingly engaged with backstop shaft 81, such as one being slidably positioned within the other. Thus, cutting blade assembly 70 also preferably has a hollow inner shaft 74 which is sized and configured such that inner shaft 74 may slide along the length of, and preferably on the outside of, backstop shaft 81. In other words, backstop shaft 81 is preferably slidably positioned within inner shaft 74 of the cutting blade assembly.

Cutting blades 71 extend away from the lower, or distal, end 75 of inner shaft 74, and preferably have an cutting edge which extends at an upward angle to shaft 71. In fact, the angle between cutting edge 72 (see FIG. 29) of each cutting blade 71 and the longitudinal axis of inner shaft 74 should correspond to the angle between each wing 84 and the longitudinal axis of backstop shaft 81. As the penetration member is advanced downwardly along shaft 81, a cutting blade 71 will penetrate tissue 40 along either side of backstop shaft 81 (see FIG. 16). As cutting blade assembly 70 is urged further downwardly, each cutting blade 71 will pass completely through tissue 40 until it contacts a wing 84, as shown in FIG. 21. Further advancement of the cutting blade assembly is prevented by wings 84, thereby limiting the depth of penetration of the cutting blades 71. In this manner, cutting blades 71 will be prevented from inadvertently piercing any anatomical structures which are located beneath tissue layer 40.

As seen in FIG. 4, each wing 84 also preferably has a groove 86 which corresponds approximately in length and width to the cutting edge of each cutting blade 71. Grooves 86 will thereby receive a cutting blade 71 therein upon full tissue penetration. In addition, once the tissue has been properly penetrated, the cutting blade assembly (i.e., the penetration member) and back stop assembly may be removed from the opening created in the tissue as a unit. As long as the cutting blade assembly is urged against wings 84, sharp edge 72 of each cutting blade 71 will be safety positioned within its respective groove 86 in a wing 84. This will further assist in preventing inadvertent injury to the patient or medical practitioners, particularly upon removal of the cutting blade assembly after cannula insertion has been completed.

Figure 10:
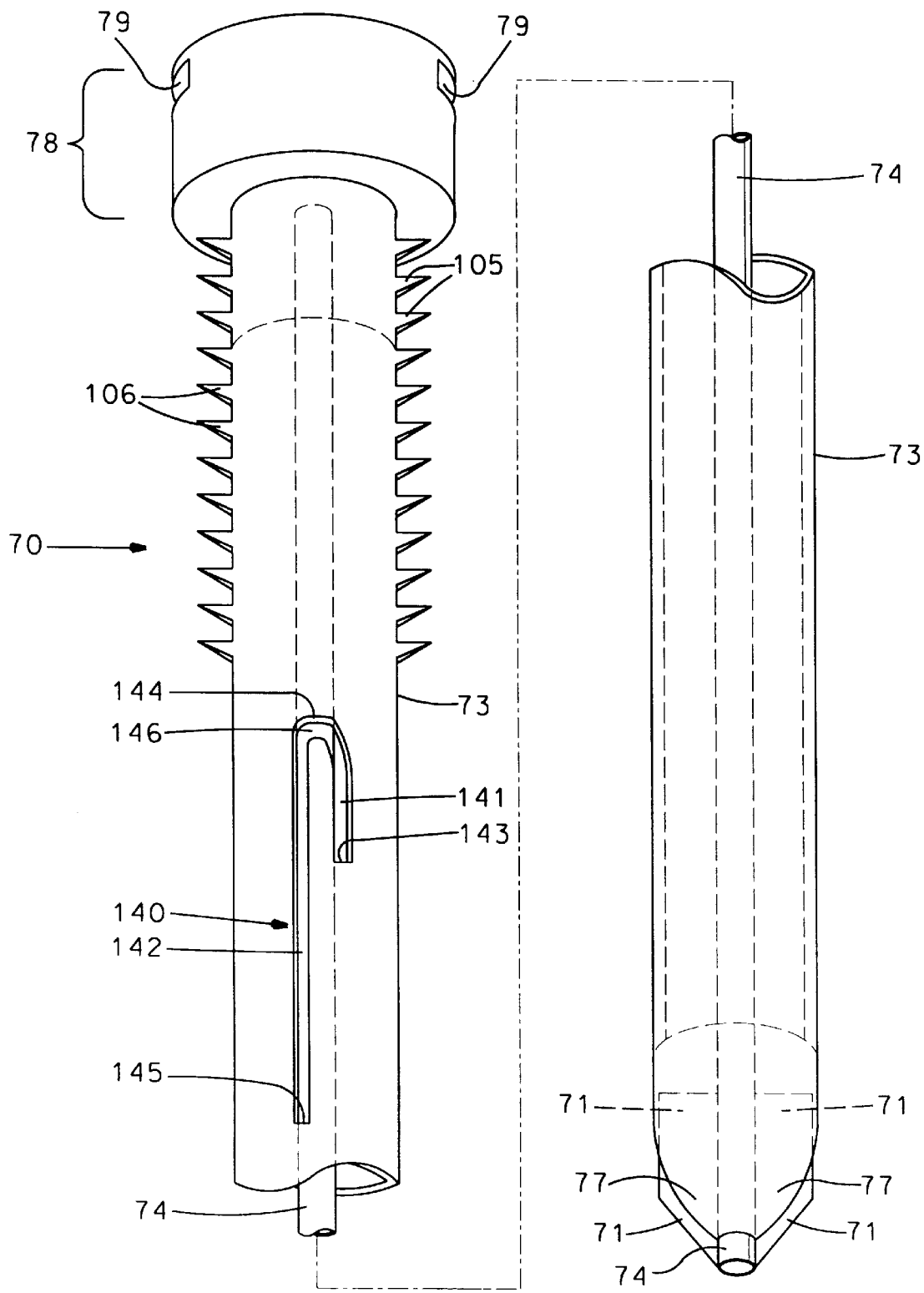
FIG. 10 is schematic side view, in partial cut-away, of the cutting blade assembly.
Figure 28:
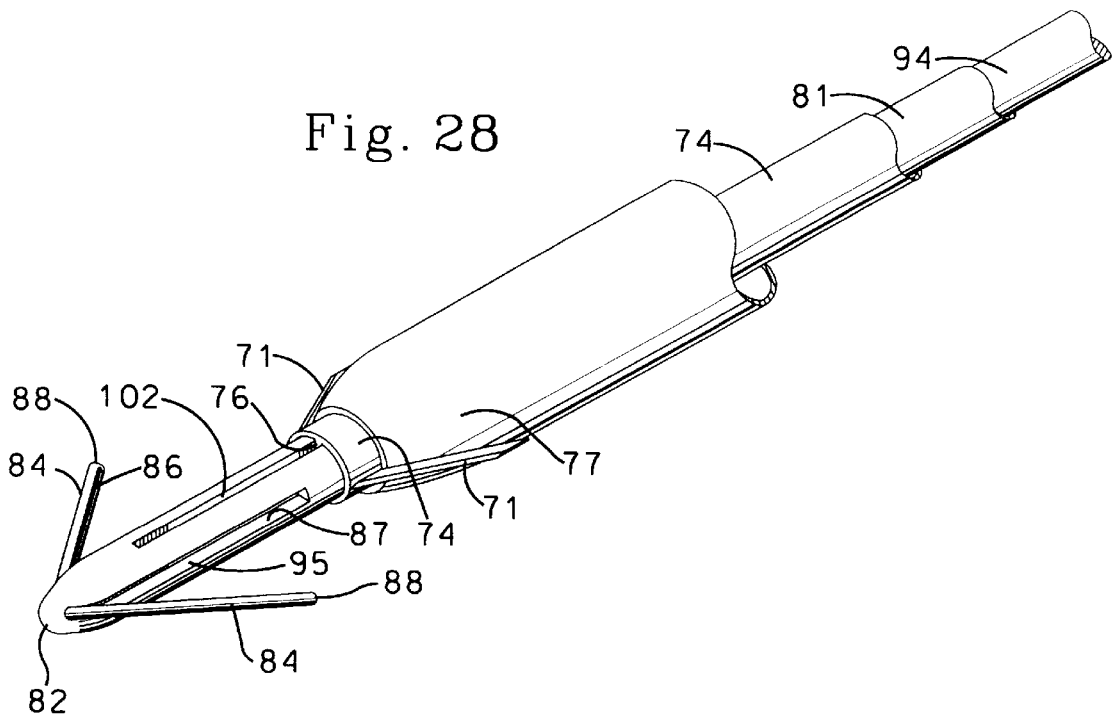
FIG. 28 is a perspective view of lower end portions of the backstop assembly and the cutting blade assembly, wherein the wing members are depicted in their initial condition (i.e., prior to passage through the tissue)
Figure 29:
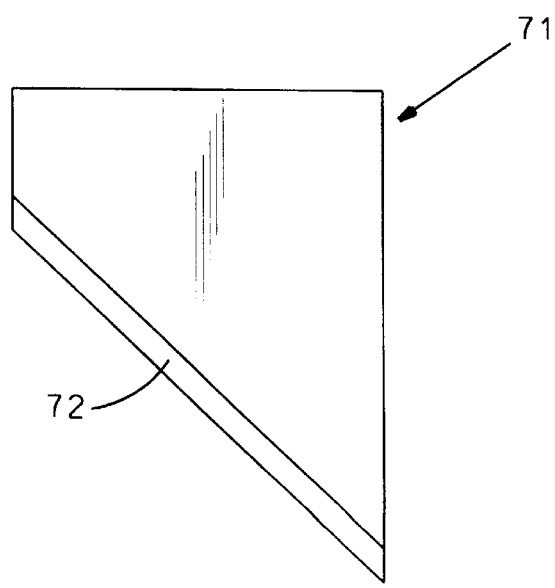
FIG. 29 is a side view of a cutting blade according to one embodiment of the present invention.

As seen in FIG. 29, each cutting blade 71 may generally comprise a thin, metal, substantially triangular-shaped element having a sharpened leading edge 72. Edge 72 and the rest of blade 71 may also taper upwardly in order to assist in enlarging the tissue opening created by edge 72. While a pair of cutting blades 71 may merely be secured to opposite sides of shaft 74 of the penetration member, such configuration will generally only result in the creation of an elongated slit through tissue 40 (with a small, central hole created by shaft 74). While such a configuration is included within the scope of the present invention, the preferred embodiment for the cutting blade assembly includes a substantially hollow, elongated body 73 extending upwardly away from lower end 75 of inner shaft 74. In fact, inner shaft 74 is positioned within body 73, as best shown in FIG. 10. While body 73 is preferably cylindrical, its distal or lower end region 77 should curvingly taper towards lower end 75 of inner shaft 74, as shown in FIGS. 10 and 28. Therefore, lower end 77 of body 73 of the penetration member will be generally bullet-shaped, with inner shaft 74 longitudinally extending from lower end 77 through the center of body 73. Cutting blades 71 are secured directly to, or even within lower end 77, as shown, such that their sharp leading edge 72 is exposed. In fact, lower end 77 of body 73 is preferably solid (except for inner shaft 74 extending therethrough) thereby rigidifying and strengthening lower end 77, as well as providing a more secure attachment of cutting blades 71 to body 73. The portion of body 73 located just beneath its upper end portion 78 may also be solid (with shaft 74 extending therethrough; FIG. 10) thereby further strengthening the cutting blade assembly.

The curvingly tapered, or bullet-shaped, configuration of lower end region 77 of body 73 serves the additional purpose of expanding the tissue opening created by cutting blades 71.

As the sharp leading edge 72 of each cutting blade 71 is urged through the patient's tissue to form a slit-like opening, the bullet-shaped lower end 77 of body 73 will gradually expand this tissue opening as lower end 77 is urged through the opening. Although this feature may not always be needed, depending upon the purpose for the creation of the tissue opening, this feature is helpful when the apparatus of the present invention is used as a trocar. Expansion of the tissue opening by lower end 77 will facilitate passage of the cannula through the tissue opening in order to provide access to the anatomical cavity.

Although the penetration member, or cutting blade assembly, may be advanced through the tissue towards the deployed backstop by a variety of means, including direct force applied by hand to the cutting blade assembly, applicant's preferred embodiment includes additional features which simplify and improve the safety of the use of the apparatus of the present invention. These additional features not only simplify the tissue penetration process, they also provide greater control over the urging of cutting blades 71 through the tissue.

As mentioned previously, backstop shaft 81 may be of a non-spherical cross-sectional shape (such as elliptical) such that backstop shaft 81 may not rotate, yet will still slide, within inner shaft 74 of the cutting blade assembly. Alternatively, as depicted in FIG. 28, a longitudinally extending guide channel 102 may be provided in the surface of back stop shaft 81, extending from a point adjacent distal end 82 of shaft 81 along a portion of the length of shaft 81. A corresponding guide tab 76 is provided on the interior of shaft 74, and extends radially inward so as to be mateable with guide channel 102. Guide tab 76 may be any of a variety of shapes, however, its cross-sectional shape should correspond to that of guide channel 102 (such as rectangular) and its length should be significantly shorter than the length of guide channel 102. In this manner, when guide tab 76 is positioned within guide channel 102, backstop shaft 81 may non-rotatingly slide within the interior of shaft 74 of the cutting assembly. An additional guide channel and guide tab may be provided on the opposite sides of backstop shaft 81 and inner shaft 74, respectively, if needed.

The apparatus of the present invention also includes a mechanical mechanism for activation and advancement of cutting blade assembly 70 along backstop shaft 81. As best seen in FIG. 10, a pair of substantially rectangular cutouts 79 are provided in body 73 of the cutting blade assembly on its upper (or proximal) end portion 78. It is also preferred that upper end portion 78 of body 73 be greater in diameter (both exterior and interior) than the rest of body 73. Inner shaft 74 of body 70 extends from lower end 77 to the juncture of body 73 and enlarged upper end portion 78. Inner shaft 74 is, however, open at this juncture such that backstop shaft 81 may be inserted therethrough.

First and second sets of ratchet teeth 105 and 106, respectively, are positioned along opposite sides of body 73 of the cutting blade assembly beneath enlarged upper end portion 78. The ratchet teeth of each set are preferably spaced evenly along body 73, and extend from just below the enlarged upper end portion 78 towards lower end 77. The upper surface of each of the ratchet teeth 105 and 106 is preferably substantially flat, extending perpendicularly away from the outer surface of body 73, while the lower surface of each ratchet tooth preferably extends at an upward angle to the surface of body 73. In this manner, each of the ratchet teeth 105 and 106 may be triangular in cross-sectional shape.

In accordance with one embodiment of the present invention, housing 60 includes mechanisms which provide for the controlled activation (or release) and advancement of the cutting blade assembly towards backstop wings 84. These mechanisms within housing 60 cooperate with cutouts 79, as well as the first and second set of ratchet teeth 105 and 106 described above. As best seen in FIG. 2, the apparatus of the present invention is initially configured such that the cutting blade assembly is secured within housing 60. Preferably, the lower portion of the solid walls of housing 60 which form release chamber 63 are nested within upper end portion 78 of the cutting blade assembly. The housing walls which form the lower portion of release chambers 63, as well as the interior diameter and length of upper end portion 78, are sized such that the housing walls will releasably nest within upper end portion 78. Since this fit is not snug, a locking mechanism is also provided to ensure that the cutting blade assembly will not be prematurely separated from chamber 63. In a preferred embodiment, this mechanism is provided by a pair of pivoting latch members 64 which are pivotally secured within housing 60, as shown in FIG. 2.

Figure 13:
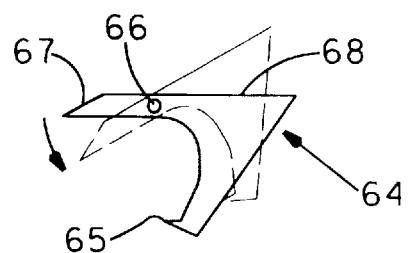
FIG. 13 is a side view of a latch member according to one embodiment of the present invention.

FIG. 13 depicts a side view of a latch member 64 in its locking position, where at latch member 64 will prevent the cutting blade assembly from being released within housing 60. When latch members 64 are in this position, the cutting blade assembly will be secured within housing 60 such that the wall forming the lower portion of release chamber 63 is nested within upper end portion 78 of the cutting blade assembly. When latch members 64 pivot to their release position (shown in FIG. 13 in dashed line), the cutting blade assembly will be released from the wall of chamber 63, thereby allowing the cutting blade assembly to be advanced downwardly towards the backstop wings. Until latch members 64 pivot to their release position, the cutting blade assembly cannot be advanced.

Each latch member 64 has an aperture 66 therethrough, and may be secured within housing 60 by means of a pin or other suitable rod-like member which extends through aperture 66. Each latch member 64 further comprises a latch hook 65, as well as an angled cam surface 67. Latch hook 65 is configured and positioned such that when the latch member is in its locked position, latch hook 65 will engage cutout 79 in upper end portion 78 of the cutting blade assembly, thereby retaining the cutting blade assembly. When latch member 64 pivots to its release position, latch hook 65 will move out of cutout 79, thereby releasing the cutting blade assembly (see FIG. 15).

Figure 12:
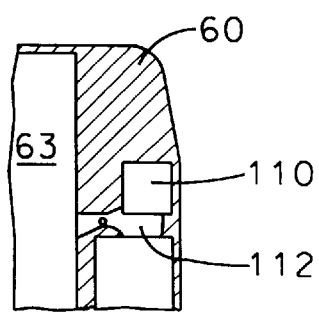
FIG. 12 is a cross-sectional view of a portion of the housing (60)

In order to prevent premature pivoting of latch members 64, and, in turn, premature release of the cutting blade assembly, each latch member 64 is preferably spring-biased towards its locking position. This spring biasing may be accomplished by any of a variety of springs, and that shown is but merely one preferred embodiment. In the embodiment shown, and as best seen in FIGS. 2 and 12, housing 60 includes a hollow cylindrical cavity 110 positioned on either side of release chamber 63. In addition, housing 60 also has cutout regions 112 positioned in communication with cavities 110, and sized and configured to accommodate portions of latch members 64 therein. Each latch member 64 also has a flat upper surface 68, (FIG. 13) and each latch member which may be positioned within cutout region 112 such that its flat upper surface 68 is located within the lower portion of chamber 110. A release spring 111, preferably a helical compression spring, is positioned within chamber 110 such that it provides a downward force against flat upper surface 68 of latch member 64, thereby spring biasing latch member 64 towards it locking position. Since latch member 64 is preferably made from thin metal sheet, it may also be necessary to provide a cylindrical washer or other suitable thrust plate between release spring 111 and flat surface 68 of latch member 64 in order to ensure that the downward force provided by release spring 111 is properly applied to the latch member.

The pivoting of latch members 64 to their open or releasing position may be accomplished by a variety of mechanisms. In a preferred embodiment, release arms 97 described previously may be employed for this purpose. Each latch member 64 should be positioned such that its angled cam surface 67 extends into release chamber 63 as shown. As best seen in FIG. 15, as piston rod 94 is urged downwardly, release arms 97 will likewise move downwardly towards cam surfaces 67 of latch members 64. As lower edge 103 of each release arm 97 moves downwardly so as to contact angled cam surface 67, latch members 64 will pivot towards their open, or releasing position. In order to further provide appropriate pivoting of the latched members, the lower edge surface 103 of each release arm 97 is also preferably angled such that its slope corresponds approximately to that of angled cam surface 67 on each latch member 64.

Latch members 64, as well as release arms 97 are also preferably configured and located such that latch members 64 will not be pivoted to their blade release position until backstop wings 84 have passed completely through the patient's tissue and redeployed to their open position (as in FIG. 15). Therefore, release arms 97 should not contact cam surfaces 67 of the latch members until piston lock pin 99 has passed into lower, or second, channel 91 at proximal end 83 of backstop shaft 81. In order to further prevent premature release of the cutting blade assembly, release of latch member 64 should not occur until piston lock pin 99 has nearly, or completely moved downwardly its full extent within second channel 91. This position corresponds to full wing redeployment, and will coincide with the audible and visual confirmation of proper wing deployment. Therefore, the release of the cutting blade assembly by latch members 64 will coincide with the visual and audible conformation of backstop wing deployment within the anatomical cavity.

Once the cutting blade assembly has been released within housing 60, a preferred embodiment of the present invention also provides a mechanism for the non-reversible, controlled advancement of the cutting blade assembly towards the backstop. In addition, the cutting blade assembly should also be prevented from dropping onto the patient's tissue 40 upon release thereof by latch members 64.

As best seen in FIG. 2, a set of anti-reversing ratchet teeth 115 are provided within housing 60. Ratchet teeth 115 are similar in shape to first set of ratchet teeth 105 provided on body 73 of the cutting blade assembly, however ratchet teeth 115 have a flat under surface and an angled upper surface. Thus, when body 73 of the cutting blade assembly moves in the downward direction, the angled undersurface of ratchet teeth 105 will contact the angled upper surface of anti-reversing ratchet teeth 115. Ratchet teeth 115 are preferably provided in an integral arrangement such that each tooth 115 is secured to, and extends away from a solid ratchet body 118. Ratchet body 118 is positioned within a spring chamber 119 provided within housing 60 at its lower end. Spring chamber 119 also preferably has a shouldered opening through which ratchet teeth 115 extend, and ratchet body 118 has corresponding shoulders on either end such that ratchet body 118 cannot escape spring chamber 119. Ratchet body 118 is spring biased towards body 73 of the cutting blade assembly, such that anti-reversing ratchet teeth 115 protrude out of spring chamber 119 towards body 73. A helical spring 116 is provided within spring chamber 119 in order to spring bias ratchet body 118 in the appropriate direction, however it will be understood that a leaf spring or other type of spring may similarly be used instead of a helical spring.

As the cutting blade assembly moves downwardly and the sloped under surface of ratchet teeth 105 contact the sloped upper surface of anti-reversing ratchet teeth 115, ratchet body 118 will be urged into spring chamber 119 as ratchet teeth 105 slide past ratchet teeth 115 (as best seen in FIG. 15). Since the spacing between individual ratchet teeth 105 and the spacing between individual anti-reversing ratchet teeth 115 are preferably equivalent, as each ratchet tooth 105 moves completely past an anti-reversing tooth 115, ratchet body 118 will be urged back towards body 73 by spring 116 (see FIG. 16). Since the upper surface of teeth 105 and the lower surface of teeth 115 are substantially flat, anti-reversing ratchet teeth 115 will then prevent upward movement of body 73. Ratchet teeth 105 provided on body 73 can only move past anti-reversing teeth 115 in the downward direction. In addition, when the cutting blade assembly is released within housing 60 by latch members 64 and drops downwardly, anti-reversing teeth 165 may also act as a brake, thereby limiting the amount to which the cutting blade assembly drops. Furthermore, after full advancement of the cutting blades through the tissue, ratchet teeth 115 will prevent the cutting blade assembly from being rearmed, since the cutting blade assembly can only move in one direction (i.e., downwardly) after a single ratchet tooth 110 has moved beyond a single anti-reversing tooth 115.

As mentioned previously, housing 60 has a handle 61 which facilitates manipulation of the apparatus of the present invention by the medical practitioner. Handle 61 may be provided in a variety of shapes, and the pistol-grip style shown is merely one possible configuration. In order to provide for advancement of the cutting blade assembly, a blade advancement arm 62 is also provided adjacent handle 61. Advancement arm 62 can likewise be provided in a variety of configurations, and that shown is but merely one preferred embodiment.

Blade advancement arm 62 may be pivotally secured to housing 60 by means of a pivot pin 125 which extends through an enlarged head portion 69 of arm 62. Enlarged head portion 69 has a flat lower surface 126, and a curved upper surface 127. Curved upper surface 127 also has a plurality of advancement teeth 128 which extend radially outward from surface 127. Advancement teeth 128 are spaced and configured so as to be engageable with second set of ratchet teeth 106 provided on body 73 of the cutting blade assembly. In this manner, once the cutting blade assembly has been released within housing 60, the cutting blade assembly will drop downwardly such that ratchet teeth 106 may be engaged by advancement teeth 128. As blade advancement arm 62 is urged towards handle 61 (such as by squeezing the two members towards each other), enlarged head portion 69 of arm 62 will rotate clockwise, which in turn results in advancement teeth 128 rotating downwardly so as to engage ratchet teeth 106. As blade advancement arm 62 is further urged toward handle 61, advancement teeth 128 will urge the cutting blade assembly downwardly towards the backstop (FIG. 15). It will be recognized that anti-reversing ratchet teeth 115 will prevent movement of advancement arm 62 in the opposite direction once the cutting blade advancement process has commenced. In addition, the enlarged head portion of advancement arm 62, as well as advancement teeth 128, should be selected and configured such that a single squeeze of arm 62 towards handle 61 will provide sufficient cutting blade advancement for penetration of the tissue wall of the anatomical cavity being penetrated.

Of course the blade actuator and advancement mechanisms shown in the attached drawings and described above is merely exemplary, as a variety of mechanisms may be employed for the same purposes. For example, a progressive ratcheting mechanism may be used wherein the cutting blade is advanced by multiple compressions of a blade advancement arm. Such a mechanism will allow the cutting blade assembly to be advanced by short, multiple squeezes of handle 61 and arm 62, with arm 62 returning to its extended position after each squeeze. Such mechanisms are employed, for example, in common caulking guns. Of course, a variety of other mechanisms may be used to advance the cutting blade assembly, including those which do not employ ratchet teeth or any type of ratcheting mechanism. Therefore, the present invention is not limited to the use of the cutting blade advancement mechanism depicted in the attached drawings and described herein.

Figure 14:
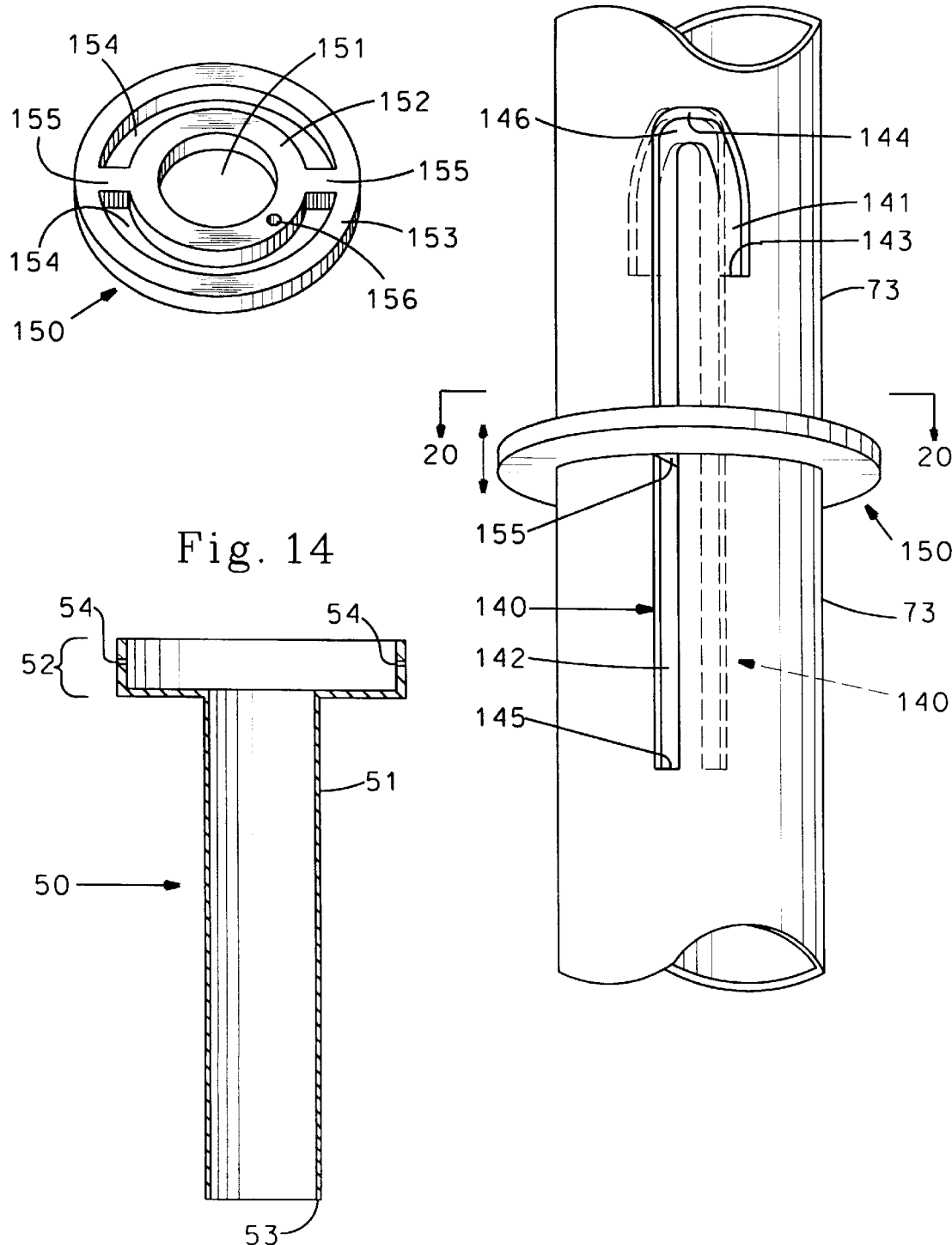
FIG. 14 is a side cross-sectional view of a cannula according to one embodiment of the present invention.

As mentioned previously, the apparatus of the present invention is particularly suited for use as a trocar, and therefore a cannula 50 is also provided. Cannula 50 (depicted in FIG. 14) includes a cannula sleeve 51, and a cannula handle (or head) portion 52. Cannula sleeve 51 is preferably substantially cylindrical in nature, and may have a flat or angled distal end surface 53. Although the dimensions of cannula 50, and in fact the dimensions of all of the components of the apparatus according to the present invention, may vary depending upon the intended use, in a preferred embodiment Cannula 50 may be between about 2.5 and about 6 cm in length. Cannula shaft 51 may have an interior diameter of between about 6 and about 21 mm, and therefore the distance across cutting blades 71 (which will correspond to the length of the tissue opening created by blades 71) should be slightly smaller (between about 5 and about 20 mm) to allow the cutting blade assembly to slide within cannula sleeve 51.

Cannula handle portion 52 may take any of a variety of shapes, and the cylindrical shape depicted is but one preferred embodiment. Cannula handle portion 52 should be larger in diameter than sleeve 51, and should also be hollow such that access to the interior of cannula sleeve 51 may be gained through the upper end of cannula handle portion 52. In fact, cannula 50 may be shaped and configured similar to cannulas provided on currently-available trocar assemblies, and may optionally include a variety of other features well-known to those skilled in the art. These additional features include various ports, with or without accompanying valves (such as a stopcock assembly), and even a flapper valve used to seal the interior of the cannula at a location within cannula handle portion 52. Such additional features are shown and described, for example, in U.S. Pat. No. 5,116,353.

A pair of slots 54 are also provided in the exterior surface of cannula handle portion 52, preferably on opposite sides thereof, adjacent its upper end. Slots 54, which may comprise rectangular slots extending completely through the wall of cannula handle portion 52, should be configured such that each is engageable by a cannula lock member, as described below.

In a preferred embodiment, cannula 50 not only serves the ultimate purpose of providing a channel through which medical instruments (such as an endoscope) may be inserted into the anatomical cavity, but also serves to shield the cutting blade assembly before and during the use of the apparatus of the present invention. When the cutting blade assembly has been released within housing 60 and drops downwardly, the anti-reversing mechanism described above will halt downward movement of the cutting blade assembly, such that cutting blades 71 will remain within cannula sleeve 51. In fact, in a preferred embodiment, cannula 50 is also released, and drops downwardly, with the cutting blade assembly such that the relationship between blades 71 and the distal end surface 53 of the cannula will remain similar to the initial state shown in FIG. 2. In fact, the cutting blade assembly and cannula are also preferably spring-biased toward the backstop, while the backstop (i.e., wings) are spring-biased upwardly towards the cannula and cutting blade assembly. This spring-biasing may even be provided by the same spring 55 (as described below), and will result in tissue layer 40 being compressed between the distal end surface 53 of the cannula and tips 88 of wings 84. In fact, when wings 84 deploy, spring 55 will provide an upward force on housing 60, and therefore backstop shaft 81, thereby helping to prevent over-penetration of the backstop shaft through the tissue. In other words, as soon as wings 84 deploy, the cutting blade assembly and cannula are released and urged downwardly by spring 55, while the backstop assembly is urged upwardly by the same spring 55, thereby preventing over-penetration of the backstop assembly.

Figure 16:
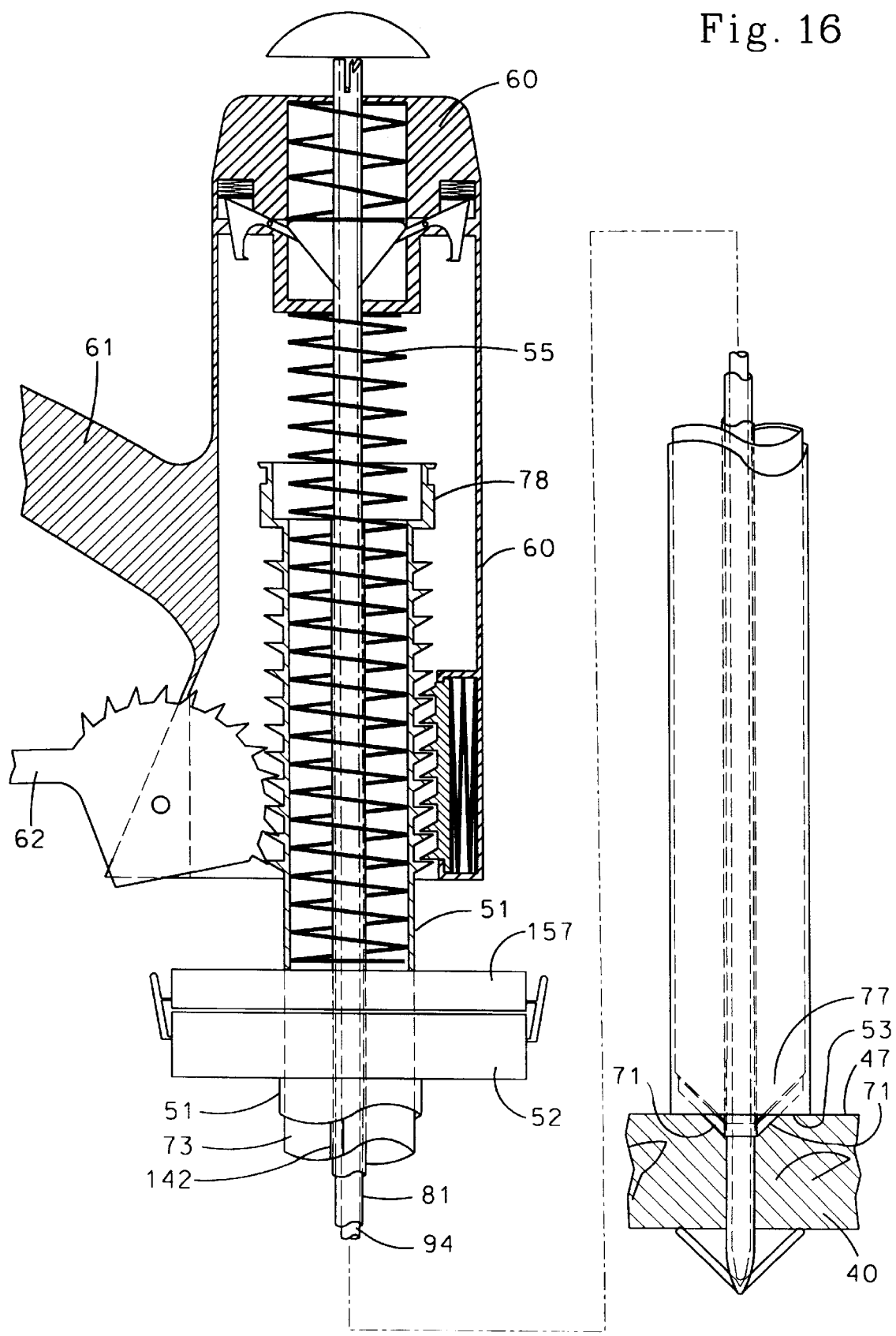
FIG. 16 is the same view as FIG. 15, however the cutting blade assembly has been further advanced so as to begin penetration of the tissue (40)

After release of the cutting blade assembly, distal end surface 53 of cannula sleeve 51 is preferably spring-biased against the tissue to be penetrated, and downward movement of the cutting blade assembly may even help urge cannula sleeve 51 to this position against outer surface 47 of tissue 40. As the cutting blade assembly is urged downwardly by means of blade advancement arm 62, cutting blades 71 will begin to penetrate tissue 40, as shown in FIG. 16. Distal end surface 53 of cannula sleeve 51, however, will remain against outer surface 47 of tissue 40 until the entire width of each cutting blade 71 has penetrated a portion of tissue 40. As mentioned previously, as cutting blades 71 are urged through tissue 40, tapered lower end 77 of the cutting blade assembly will begin to expand the slit created in the tissue by the cutting blades. Since the exterior diameter of cannula sleeve 51 is preferably only slightly greater than the maximum diameter of lower end 77 of the cutting blade assembly which is moving through the interior of cannula sleeve 51, once lower end 77 has expanded the tissue opening downward pressure on cannula 50 will urge its distal end surface 53 through the tissue opening (as seen in FIG. 21). In fact, once cutting blade 71 has passed completely through tissue 40 so as to contact backstop wings 84, cannula sleeve 51 may be readily urged through the tissue opening thus created, since tapered lower end 77 will have sufficiently expanded the tissue opening to allow cannula penetration. The result is that cannula sleeve 51 will extend completely through the tissue opening into the anatomical cavity (FIG. 22). At this point, the entire cutting blade assembly and backstop assembly may be removed from the cannula by means of housing 60, thereby leaving only cannula 50 in place.

While once again simple hand force may be used to urge cannula 50 downwardly through the tissue opening, the apparatus of the present invention may also provide for automatic cannula deployment. In fact, downward movement of the cutting blade assembly results in a corresponding downward movement of cannula 50. Preferably, however, the cutting blade assembly and cannula 50 do not move in a manner completely dependent upon one another, since it is preferred that cutting blades 71 only advance beyond the distal (or lower) end surface 53 of the cannula after distal surface 53 is against outer surface 47 of tissue 40.

Cutting blades 71 should remain within cannula sleeve 51, therein guarded, until this stage has been reached. Thereafter, cutting blade assembly 70 should advance along backstop shaft 81 independently of cannula 50 in order to penetrate tissue 40. While cutting blades 71 are urged through the tissue, however, cannula 50 should be urged downwardly such that once the tissue opening has been created by blades 71 and sufficiently expanded by lower end 77 of the cutting blade assembly, cannula sleeve 51 will be urged through the expanded tissue opening.

In a preferred embodiment of the present invention, blade advancement arm 62 (as previously described) is employed to urge the cutting blade assembly in the downward direction. Cannula 50 is preferably spring-biased in the downward direction, and is also preferably released in conjunction with the release of the cutting blade assembly by latch members 64. In this manner, when the cutting blade assembly and cannula are released by latch members 64, cannula 50 will be urged downwardly against outer surface 47 of tissue 40 due to the spring biasing. In a preferred embodiment, this spring biasing of cannula 50 is provided by cannula spring 55 (FIG. 2). It is further preferred that cannula spring 55 also act upon the cutting blade assembly such that when the cutting blade assembly is released by latch members 64, cannula spring 55 will also urge the cutting blade assembly in the downward direction. Although cannula 50 should be urged downwardly until its distal end surface 53 contacts outer surface 47 of tissue 40, the cutting blade assembly should remain protected within cannula sleeve 51. While the anti-reversing mechanism described previously will assist in limiting downward movement of the cutting blade assembly, cannula spring 55 should also not urge the cutting blade assembly downwardly beyond distal end surface 53 of cannula 50. This will ensure that the cutting blades remain guarded by the cannula and that advancement arm 62 may controllably advance the blades through the tissue. Therefore, cannula 50 should also be capable of moving independently of cutting blade assembly 70.

As shown in FIG. 10, body 73 of cutting blade assembly 70 has a double-channeled slot 140 positioned between the ratchet teeth (105 and 106) and lower end 77. In fact, a pair of double-channeled slots 140 are preferably provided on opposite sides of body 73 in substantially identical locations and orientations (FIG. 17). Double-channeled slot 140 includes a first (or short) channel 141, and a second (or long) channel 142 positioned adjacent and to the left of first channel 141. In addition, double-channeled slot 140 extends completely through the outer wall of body 73, such that inner shaft 74 is visible therethrough. A short, connector channel 146 provides communication between first and second channels 141 and 142, and is positioned at the upper end of said first and second channels. In this manner, a member extending through first channel 41 may move upwardly therein, laterally across connector channel 146, and thereafter downwardly within second channel 142. First channel 141 also includes a lower end wall 143, and second channel 142 similarly has a lower end wall 145. Connector channel 146 has an upper wall 144.

FIG. 18 depicts thrust washer 150 which, in cooperation with double channel ed slot 140, will transfer force from cannula spring 55 to cannula 50, as well as cutting blade assembly 70. Thrust washer 150 has a cylindrical bore 151 through its center which is provided by the interior of inner ring 152. An outer ring 153 is also provided on thrust washer 150 such that an annular space 154 is provided between inner ring 152 and outer ring 153. A pair of arms 155 extend radially inward from outer ring 153, thereby connecting outer ring 153 to inner ring 152.

Figure 20:
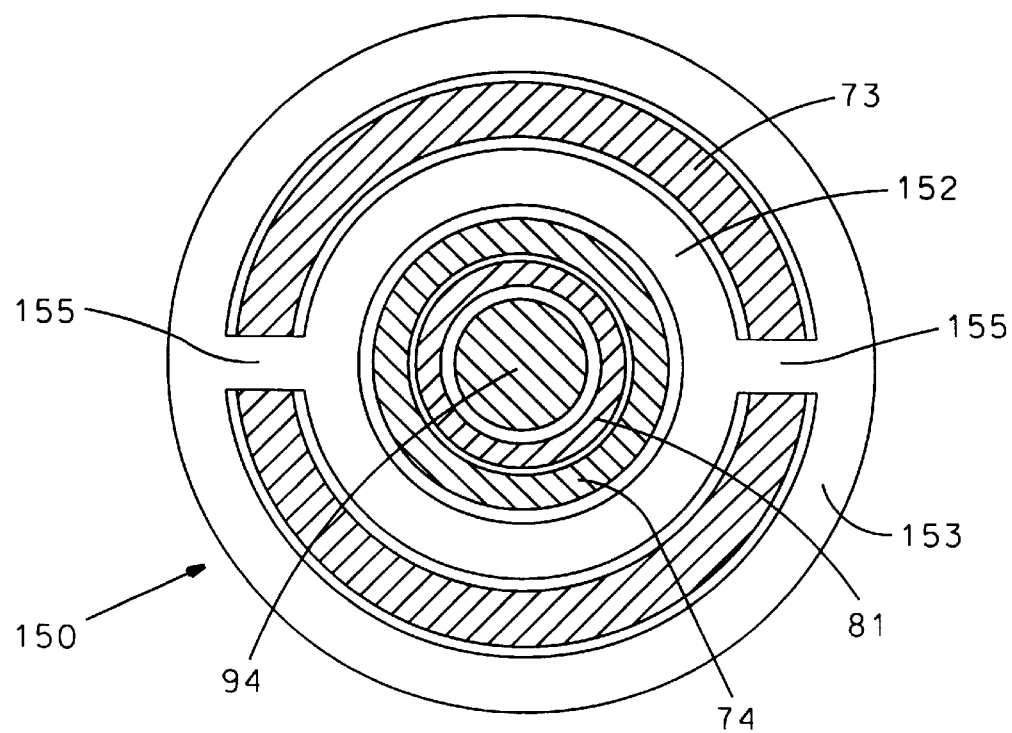
FIG. 20 is a cross-sectional view of FIG. 17, taken along line 20—20 thereof.

FIGS. 17 and 20 depict the manner in which thrust washer 150 is positioned on the apparatus of the present invention. Inner ring 152 is sized such that bore 151 is slightly greater in diameter than inner shaft 74 of the cutting blade assembly. Thrust washer 150 is thus positioned such that inner shaft 74 of cutting blade assembly 70 is slidably positioned within bore 151 (as best shown in FIG. 20). Inner ring 152 and outer ring 153 of thrust washer 150 are also preferably sized such that body 73 of the cutting blade assembly may be slidably positioned within annular space 154 of washer 150, with washer arms 155 extending inwardly through double-channeled slots 140. When positioned in this manner, arms 155 of thrust washer 150 may travel within double-channeled slot 140, including both its first and second channels 141 and 142, respectively. Washer 150 may thereby slide along the exterior of body 73 of the cutting blade assembly, with its extent of travel defined and limited by double-channeled slot 140. It should be noted that washer 150 may be positioned as shown by manufacturing body 73 of the cutting blade assembly 70 in two identical halves which are joined and secured to one another at a seam which extends though both double-channeled slots 140. In this manner, washer 150 may be positioned within slots 140 before assembly of the two halves of body 73.

Figure 19:
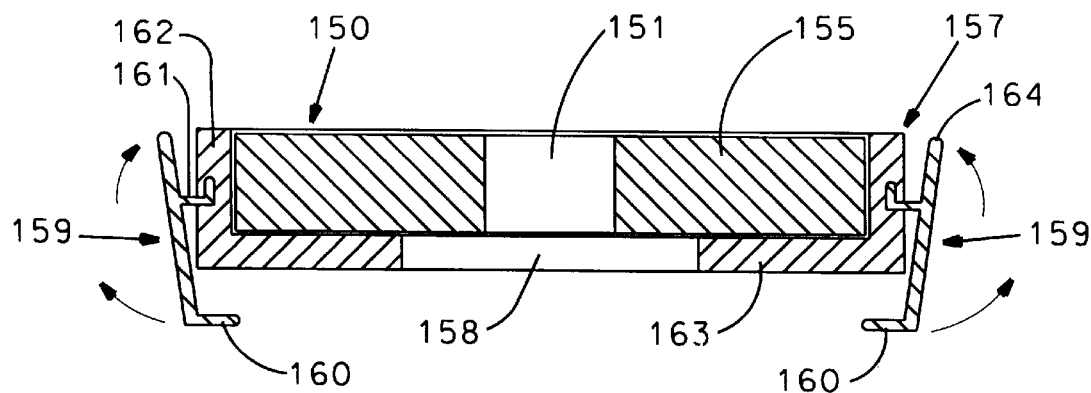
FIG. 19 is a side cross-sectional view of the thrust washer positioned in the thrust washer housing (157)

FIG. 19 is a side, cross-sectional view of a thrust washer housing 157 which essentially comprises a cylindrical tray within which thrust washer 150 may be secured. Housing 157 includes an upright sidewall 162 having a height at least as great as thrust washer 150, and a flat bottom wall 163 having a bore 158 extending therethrough. Bore 158 should be sized so as to slidingly receive body 73 of the cutting blade assembly therein. A pair of cannula locks 159 are provided on opposite sides of washer housing 157, and each includes an elongate finger 160 which is spaced beneath bottom wall 163 and extends inwardly. Cannula locks 159 are secured to housing 157 by means of a connector arm 161 which is embedded in sidewall 162 of housing 157. Since housing 157 and cannula locks 159 may be made, for example, from molded plastic, connector arms 161, as well as the remaining portions of cannula locks 159 may be integrally molded with housing 157. Connector arms 161 should be sufficiently thin so as to be resiliently flexible. In this manner, when upper end 164 of each cannula lock 159 is pressed inwardly towards the sidewall 162 of housing 157, elongate fingers 160 will move in the direction of the arrows shown in FIG. 19 (i.e., outwardly). Cannula locks 159 may be pivotally attached to housing 157 in a variety of other manners, and they may even be spring biased towards their cannula locking position shown in FIGS. 2 and 19.

As best seen in FIG. 2, thrust washer housing 157 may be detachably secured to cannula handle portion 52 by means of cannula locks 159. Elongate fingers 160 on cannula locks 159 are configured such that they may extend into slots 54 provided on cannula handle 52. When positioned in this manner, elongate fingers 160 will lock housing 157 to cannula handle 52. When the upper ends 164 of cannula locks 159 are depressed inwardly, however, fingers 160 will move out of slots 54 on the cannula handle, thereby releasing the cannula from thrust washer housing 157.

As also shown in FIG. 2, cannula spring 55 is preferably helical in nature, and is positioned within the interior of body 73 of the cutting blade assembly with inner shaft 74 extending through the center of spring 55. The upper end of spring 55 bears against that portion of housing 60 which forms the bottom wall of release chamber 63. The lower end of helical cannula spring 55 bears against the upper surface of inner ring 152 of thrust washer 150. In its initial condition (i.e., before the apparatus of the present invention has been activated or deployed in any manner), spring 55 will be in a compressed state, thereby spring-biasing thrust washer 150, and in turn housing 157 and cannula handle 52, downwardly. Since thrust washer housing 57 is releasably attached to cannula handle 52, any force applied to thrust washer 150 (such as by spring 55) will be imparted to the entire cannula assembly.

In this initial state, thrust washer 150 is also positioned within double-channeled slot 140 of the cutting blade assembly such that arms 155 of the washer are positioned within the first (or short) channel 141 of the double-channeled slot. Since spring 55 spring-biases thrust washer 150 in the downward direction, the underside of arms of 155 will bear against lower wall 143 of first channel 141. In this manner, spring 55 will also bias the cutting blade assembly in the downward direction, since the downward force acting on thrust washer 150 will be imparted to the cutting blade assembly through lower wall 143 of the double-channeled slot. Therefore, when the cutting blade assembly is released by latch members 64, cannula spring 55 will urge the cutting blade assembly and the cannula in the downward direction until distal end surface 53 of cannula sleeve 51 contacts outer surface 47 of the tissue being penetrated. At the same time, backstop shaft 81, and in turn backstop wings 84, will be urged upwardly towards and against interior surface 48 of the tissue. This simultaneous traction on the backstop assembly and countertraction on the cannula/penetration member will significantly reduce the possibility that the backstop member is inserted too far into the anatomical cavity, since the traction/countertraction will occur as soon as the backstop wings are deployed within the anatomical cavity. The surgeon may then begin advancing the cutting blade assembly using arm 62 in the manner previously described, and as shown in FIG. 15. Spring 55 will continue to provide traction on the backstop assembly (through housing 60), and this traction will further assist in blade penetration through the tissue (since the tissue is pulled into the advancing blades by the backstop wings).

Since further advancement of the cannula is prevented by distal end surface 53 being urged against outer surface 47 tissue 40, it will be recognized that as the cutting blade assembly is advanced downwardly, washer 150 will begin to travel upwardly within first channel 141 of the double-channeled slot provided on the cutting blade assembly. As advancement of the cutting blade assembly is continued, cutting blades 71 will eventually protrude beyond distal end surface 53 of the cannula as shown in FIG. 16. Advancement of cutting blades 71 beyond lower distal end surface 53 of the cannula will be limited by the fact that thrust washer 150 will bear against upper wall 144 of double-channeled slot 140 on the cutting blade assembly. The cutting blade assembly may not move further downwardly unless cannula 50 is also able to move in that same direction. Therefore, the distance between lower wall 143 of first channel 141 and upper wall 144 will correspond to the distance that cutting blades 71 may travel from their initial position shown in FIG. 2, to a position whereat cutting blades 71 extend just beyond lower distal end surface 53 of the cannula.

Once cutting blades 71 are extending just beyond distal end surface 53 of the cannula, with thrust washer 150 bearing against upper wall 144 of the double-channeled slot, it will be recognized that further advancement of the blade will also urge the cannula in the downward direction. In this manner, as cutting blades 71 penetrate the tissue, and this tissue opening is expanded by lower end 77 of the cutting blade assembly, cannula sleeve 51 will be urged through this opening by means of the force applied to blade advancement arm 62. Thus, further compression of arm 62 will continue to urge cutting blade 71, as well as cannula sleeve 51, through the tissue, with distal end surface 53 of cannula sleeve 51 trailing closely behind cutting blades 71.

Thrust washer 150, and in turn washer housing 157 and cannula 150, should be rotated slightly in a clockwise direction in order to position arms 155 of the washer at the top of second channel 142 after the washer has traveled upwardly to meet upper wall 144. This may be accomplished by a variety of mechanisms, however it is preferred that thrust washer 150 be spring-biased in a clockwise direction. For example, in much the same manner that helical spring 100 (FIG. 27) imparts rotational force to release arms 97, helical cannula spring 55 may have a downwardly extending tail. This downwardly extending tail may be secured within an aperture 156 provided on inner ring 152 of the washer (as shown in FIG. 18). Therefore, by merely loading cannula spring 55 in the counterclockwise direction, thrust washer 150 will be spring-biased in the clockwise direction. When washer 150 has traveled to the top of first channel 141 so as to abut against upper wall 144, cannula spring 55 will cause washer 150 to rotate slightly in a clockwise direction such that arms 155 will be positioned at the top of second channel 142 of each double-channeled slot 140. It will be recognized that the upper end of cannula spring 55 should be secured to the lower wall portion of release chamber 63 of housing 60 to ensure proper rotational biasing. Therefore, spring 55 may be glued to this wall, or a similar upwardly-extending tail may even be provided on spring 55 and secured within a suitable aperture within the lower wall of release chamber 63.

Once cutting blades 71 have reached backstop wings 84, further advancement of the cutting blade assembly (either downwardly or upwardly) will not be possible. However, since thrust washer 150 has now rotated to the top of second channel 142, cannula spring 55 will continue to urge thrust washer 150, and in turn cannula 150, in the downward direction. Since cutting blades 71 have now passed completely through the tissue to be penetrated, this downward force on the cannula will urge the lower distal end surface 53 of the cannula through the tissue opening, as shown in FIG. 22. Once this has been accomplished, the cannula may be released from washer housing 157 by depressing cannula locks 159. The entire cutting blade assembly, backstop assembly and housing may thereafter be easily removed from the cannula, leaving the cannula in place within the tissue opening in order to provide access to the anatomical cavity (FIG. 23). The removed apparatus should be discarded, since the preferred embodiment is intended for one-time use. One added benefit of the backstop feature of the present invention is that cutting blades 71 will extend into grooves 86 provided on each wing 84, thereby providing a blade guard which will prevent inadvertent injury to the patient or medical practitioners.

In many surgical procedures, it is often necessary to insert multiple cannulas into the patient. In addition, after one cannula has been inserted, it may also be necessary to pass other instruments through tissue, particularly through the tissue wall of an anatomical cavity. Although the apparatus described above may be used for insertion of these additional (or secondary) cannulas, or for the passage of an instrument through the tissue wall, the present invention includes an alternative, and simpler embodiment which may be used in accordance with the broad methods of the present invention.

Figure 30:
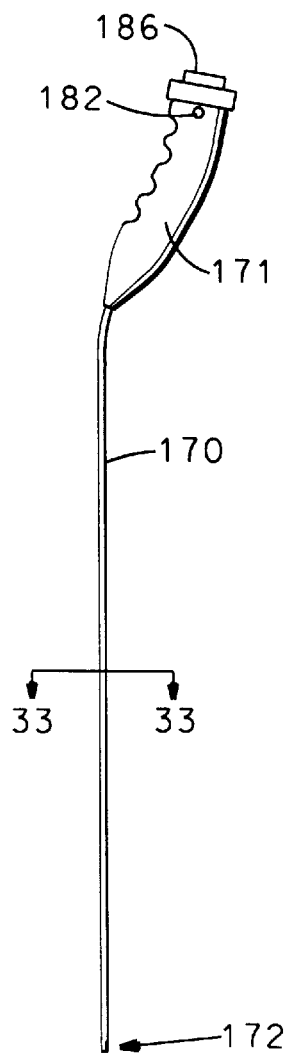
FIG. 30 is a side schematic view of an alternative embodiment for a backstop assembly according to the present invention.

FIG. 30 depicts a backstop apparatus for use in the procedures of the present invention, and comprises an elongate shaft 170 having a handle 171 secured at one end thereof. Handle 171 may be provided in a variety of shapes, and the ergonomic configuration shown is merely exemplary. In addition, handle 171 is preferably attached to shaft 170 in an offset manner in order to facilitate manipulation of the apparatus during use. Offsetting of handle 171 may be provided, for example, by a suitable bend in shaft 170, or by a variety of other means.

Figure 31:
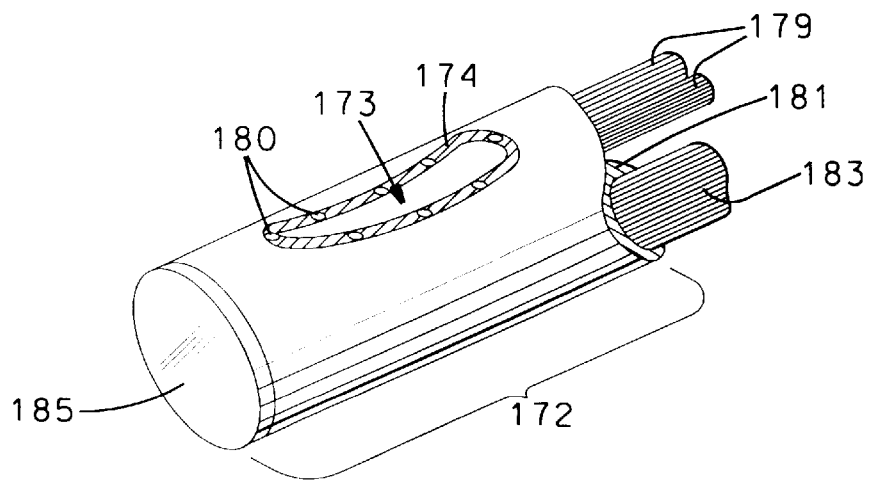
FIG. 31 is a schematic perspective view of the distal end portion of the apparatus shown in FIG. 30.

The distal end portion 172 of the backstop apparatus depicted in FIG. 30 (i.e., that end of shaft of 170 opposite the end to which handle 171 is attached) is configured such that it may act as a backstop for a penetration member. FIG. 31 is a perspective view of distal end portion 172 of shaft 170. Distal end portion 172 may be positioned within an anatomical cavity against the tissue wall to be penetrated. A penetration member, such as the obturator tip of a trocar or even a needle, may then be urged through the tissue wall until it abuts against distal end portion 172. In this manner, distal end portion 172 will act as a backstop which prevents over-insertion of the penetration member, thereby preventing inadvertent injury to the patient.

Although distal end portion 172 may take a variety of shapes, including a simple flat wall, it is preferred that a hollow cavity 173 be provided in distal end portion 172. Since shaft 170 is preferably cylindrical in nature, and since distal end portion of 172 of shaft 170 is also preferably hollow, backstop cavity 173 may be provided merely by cutting away a portion of the exterior wall of shaft 170. In the embodiment shown, the wall of shaft 170 has been cut in an elliptical manner, thereby providing an elliptical wall opening 174 which provides access to hollow cavity 173. The size of this elliptically-shaped entrance to hollow cavity 173 may vary depending upon the intended use of the apparatus.

Figure 32:
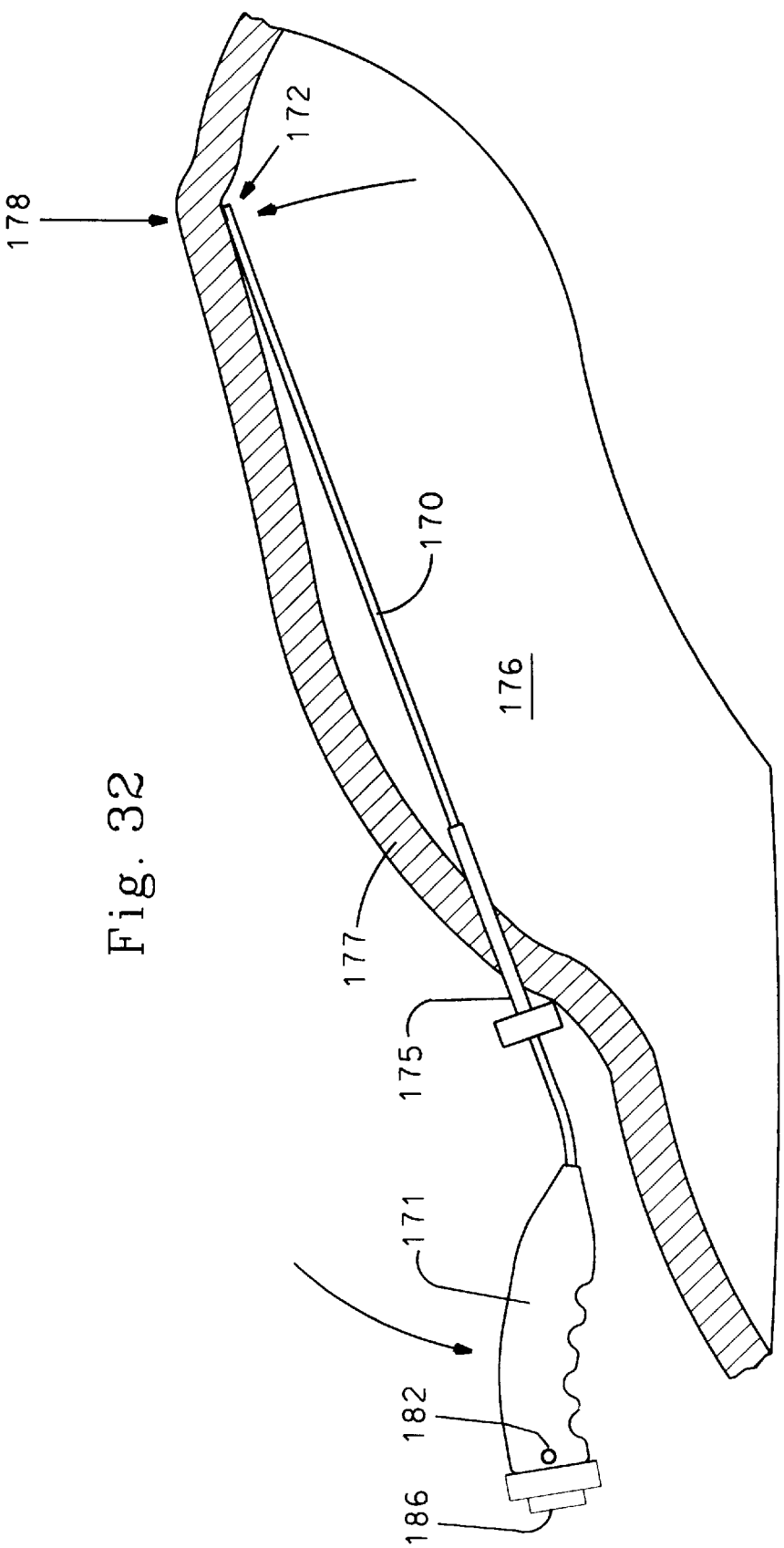
FIG. 32 is side view taken adjacent the midline of a patient, wherein a cannula (175) has been inserted through the umbilicus to provide surgical access to the abdominal cavity, and the backstop assembly has been inserted through the cannula and pivoted such that the backstop is positioned against, and pushes upwardly on the interior wall of the abdominal cavity.

FIG. 32 depicts one manner in which the backstop apparatus of FIG. 30 may be used. In this example, a primary cannula 175 has previously been inserted into an anatomical cavity 176, through tissue wall 177. The anatomical cavity may comprise, for example, the abdominal cavity of a patient, with primary cannula 175 extending through the umbilicus. Shaft 170 of the backstop apparatus of the present invention is then inserted through cannula 175 into the anatomical cavity. Thereafter, the surgeon manipulates shaft 170 using handle 171 so as to position distal end portion 172 against tissue wall 177 at a tissue penetration site 178 which is spaced away from the opening through which cannula 175 passes.

When distal end portion 172 is at the desired location, the surgeon may then apply downward pressure on handle 171, thereby moving distal end portion 172 upwardly. Since tissue wall 177 is inherently flexible, it will be recognized that cannula 175 may be manipulated considerably such that it may extend at a very shallow angle to tissue wall 177, as shown in FIG. 32. Cannula 175 will therefore act as a fulcrum for the backstop assembly, urging distal end portion 172 against the interior surface of tissue wall 177 at penetration site 178 when handle 171 is urged downwardly in the direction shown. Further downward pressure on handle 171 will allow distal end portion 172 to cause the tissue at location 178 to protrude upwardly. This tenting-up of this portion of tissue wall 177 will be readily visible, and will provide a target for insertion of a penetration member (such as the sharp bladed tip of a trocar assembly). The surgeon may then urge the penetration member through tissue wall 177 at location 178 into the backstop (e.g., backstop cavity 173), thereby preventing over-penetration.

In order to facilitate use of the backstop apparatus of the present invention, various means for providing further external indication of the location of distal end portion 172 of shaft 170 may be provided. For example, a plurality of protrusions may be provided in elliptical wall opening 174 of shaft 170 about the periphery of opening 174. When distal end portion 172 is urged against the tissue wall from within the anatomical cavity, these protrusions will help further define the elliptical entrance to hollow cavity 173.

Alternatively, and as presently preferred, the backstop apparatus of FIG. 30 includes a means for projecting light away from distal end portion 172. Preferably, light is projected upwardly away from the periphery of elliptical opening 174 in shaft 170. The light should be of sufficient strength such that when distal end portion 172 is positioned against tissue wall 177 at location 178, light projected away from elliptical opening 174 will pass through tissue wall 177 in order to be visible to the surgeon. In a preferred embodiment, the light is projected away from multiple points about the periphery of elliptical opening 174, or even as a continuous light source extending around the entire opening 174, such that the projected light will readily define the periphery of elliptical opening 174. In addition, it is also preferred that the projected light have a wavelength of between about 600 and 700 nm, since light of this wavelength will further delineate any blood vessels or other structures within the tissue wall which must be avoided. Light of the preferred wave length range is absorbed by blood, yet has high transmittance by muscle and skin with minimal scatter. Thus, the blood vessels will be clearly delineated. Therefore, the surgeon may manipulate shaft 170 using handle 171 to position hollow cavity 173 at a location which avoids blood vessels and other structures. In this manner, the apparatus of FIG. 30 also provides a way for the surgeon to avoid blood vessels and other anatomical structures during insertion of a penetration member through tissue.

The means for projecting light away from distal end portion 172 can take a variety of forms. For example, a plurality of light emitting diodes ("LED's") may be embedded in or adjacent to elliptical wall opening 174, and may be covered by clear panels (made from, e,g., acrylic). Electrical conductors for powering the LED's may extend through the interior of shaft 170 into handle 171. Within handle 171, an electrical power source, such as a simple battery, may be positioned within handle 171 in order to provide electrical power to the LED's. Alternatively, an external power source may be attached to handle 171 in electrical communication with the LED's.

Figure 33:
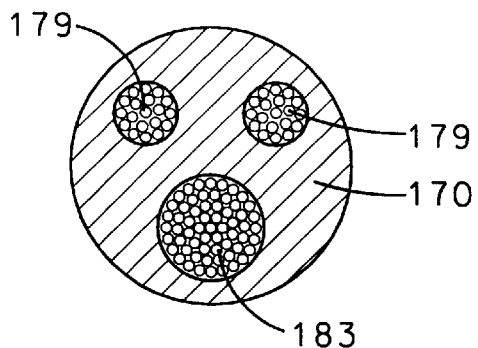
FIG. 33 is a cross-sectional view of the apparatus in FIG. 30, taken along the line 33—33 thereof.

In an alternative, and presently preferred embodiment, one or more (preferably two) fiber optic bundles may extend through shaft 170 from handle 171 to distal end portion 172, and are configured for transmitting light through shaft 170 towards end portion 172, and thereafter away from end portion 172. As shown in the cross-sectional view of shaft 170 provided in FIG. 33, a pair of light-transmitting fiber optic bundles 179 extend through shaft 170 in a spaced-bar relationship. At distal end portion 172, each of the fiber optic bundles 179 is split and routed towards terminal locations positioned in the wall of shaft 170 which forms elliptical opening 174. At a plurality of locations within the wall of shaft 170, clear, protective panels 180 (made from, e.g., acrylic) are each secured to an aperture which extends through the wall of shaft 170 at elliptical opening 174 (in or adjacent to wall opening 174).

Figure 34:
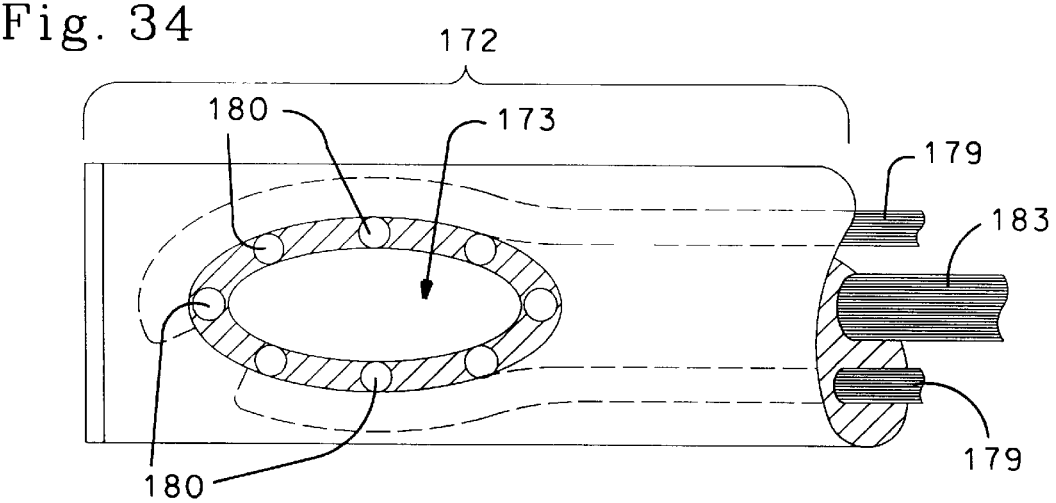
FIG. 34 is a top schematic view of the distal end portion of the apparatus shown in FIG. 30.
Figure 35:
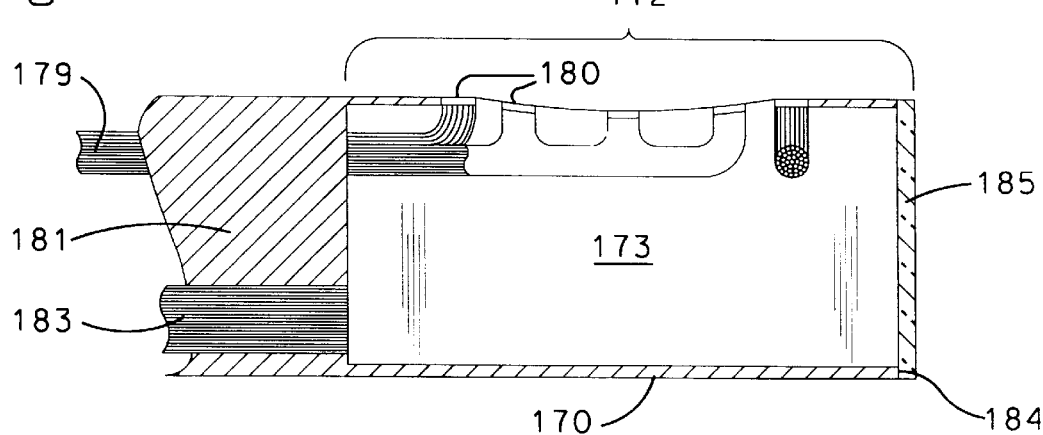
FIG. 35 is a schematic, cross-sectional view of the distal end portion one embodiment of the apparatus of FIG. 34.

In the embodiment shown in FIG. 35, wherein distal end portion 172 of shaft 170 is completely hollow, the apertures within which clear panels 180 are positioned extend into hollow cavity 173. Each of the fiber optic bundles 179 also extend into hollow cavity 173, and each is thereafter subdivided into smaller bundles having one or more optical fibers, such that one of these smaller bundles (i.e., a portion of the fibers comprising each fiber optic bundle 179) is directed to each of the various apertures underlying clear panels 180. The routing of the optical fibers can be accomplished in a variety of patterns, and that shown is merely exemplary. For example, in FIG. 34, eight clear panels 180 are embedded in the elliptical wall opening 174, with corresponding apertures extending therebeneath into hollow cavity 173. As viewed from above in FIG. 34, the upper-most fiber optic bundle 179 is subdivided into four separate, and smaller bundles of optical fibers, and each of these bundles is directed to one of the three uppermost clear panels 180, as well as the foremost clear panel 180 (i.e., that which is positioned nearest to the end of shaft 170). Similarly, the lowermost fiber optic bundle 917 is subdivided into four smaller bundles of optical fibers, which are each separately routed to one of the lowermost clear panels 180, as well as the rearmost clear panel 180 (i.e., that which is situated nearest handle 171).

In the alternative embodiment of FIG. 35, the distal end portion of shaft 170 is not completely hollow, but rather is solid in the region 181 located about the periphery of hollow cavity 173. In this manner, the optical fibers are embedded in solid region 181 of the distal end portion of the shaft. Clear panels 180, which may alternatively comprise lens elements for focusing light projected therethrough are positioned in a manner similar to that shown in FIG. 34.

While the above-described embodiments for the light-emitting feature of the present invention are presently preferred, it will be understood that various other alternative embodiments may also be effectively employed. For example, instead of a plurality of discrete point light sources (provided by clear panels 180), the entire elliptical wall opening 174 may project light upwardly away from distal end portion 172. When such a configuration is employed, the surgeon will observe a continuous ring of light for targeting tissue penetration. Such a configuration can be provided, for example, by positioning a plurality of optical fibers such that the optical fibers terminate in a continuous ring extending about the periphery of elliptical wall opening 174. Of course, a variety of other embodiments and configurations may be used for projecting light upwardly away from distal end portion 172, and all are within the scope of the present invention.

Within handle 171, fiber optic bundles 179 may be attached to a suitable light source provided therein. Alternatively, and as presently preferred, fiber optic bundles 179 extend into hollow handle 171 to light port 182. Light port 182 may comprise any of a variety of well-known connectors used for attaching optical fibers to a light source. Light port 182 provides communication between a light source and the optical fibers, thereby allowing light emitted from the light source to be transmitted through the optical fibers towards distal end portion 172.

Figure 36:
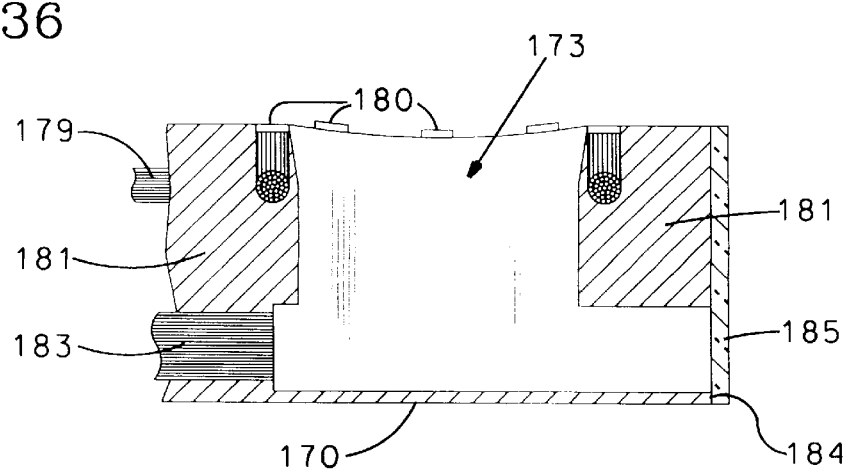
FIG. 36 is a schematic, cross-sectional view of the distal end portion of an alternative embodiment of the apparatus of FIG. 34.

A preferred embodiment of the backstop apparatus of FIGS. 30–36 also includes a third fiber optic bundle 183 which may be employed for transmitting video signals (as light). Video fiber optic bundle 183 likewise extends through shaft 170, and may be configured in relation to the other fiber optic bundles 179 in the manner shown in FIG. 33. At distal end portion 172, video fiber optic bundle 183 preferably terminates before hollow cavity 173 as shown in FIGS. 35 and 36. In addition, a lens 185, or other clear, light-transmitting cover is attached to the distal end wall 184 of shaft 170 as shown. Within handle 171, video fiber optic bundle 183 is attached to video port 186 which in turn may be attached to a video display device in a manner well-known to those skilled in the art. For example, video port 186 may be similar to video ports provided on currently-available endoscopes, and may thereafter be connected to the very same video apparatus which are presently employed with such endoscopes. In this manner, when the backstop apparatus of FIGS. 30–36 is employed, the video apparatus attached to video port 186 will provide an image of the region of the anatomical cavity which is opposite lens 185. This video image may be used by the surgeon to manipulate the backstop apparatus to the desired location. In addition, since fiber optic bundle 183 terminates before hollow cavity 173, and since cavity 173 preferably extends downwardly such that it includes the region between lens 185 and the termination of video fiber optic bundle 183, the surgeon can also readily observe a penetration member which is urged through the tissue into hollow cavity 173. For example, a video image depicting the sharp tip of a trocar which has passed through the tissue wall at the precise, desired location, will become visible as it passes into hollow cavity 173. This video image will assist the surgeon in ensuring proper trocar penetration.

The foregoing description of preferred embodiments is by no means exhaustive of the possible variations of the present invention, and has therefore been provided only for purposes of illustration and description. Modifications, variations and additions to the foregoing specific examples will be readily apparent to those skilled in the art in light of the teachings provided above, and are all well within the scope of the present invention. Thus, it is intended that the scope of the present invention be defined by the claims provided below, and not by any of the specific embodiments shown in the drawings and/or described above.

What we claim is:

1. An instrument for the penetration of tissue, comprising:
   (a) a backstop assembly having a shaft and a backstop; and
   (b) a penetration member slidingly engaged with said backstop shaft, and configured for penetrating tissue;
   said backstop assembly and said penetration member configured such that said backstop may be positioned adjacent tissue to be penetrated, such that as said penetration member is urged through the tissue along said backstop shaft, said backstop will limit the depth of penetration of said penetration member through the tissue.

2. The instrument of claim 1, wherein said penetration member includes a shaft and at least one cutting blade, and wherein said backstop shaft is slidably positioned at least partially within the shaft of said penetration member such that the shaft of said penetration member may slide along the exterior of said backstop shaft.

3. The instrument of claim 2, wherein said backstop is provided at a distal end of said backstop shaft, and wherein said at least one cutting blade is provided at a distal end of the shaft of said penetration member, said backstop shaft positioned within the shaft of said penetration member such that one or both of said cutting blade and said backstop may be advanced towards the other until the cutting blade contacts said backstop.

4. The instrument of claim 1, wherein said backstop is movable between open and closed positions, and is configured such that said backstop will limit the depth of penetration of said penetration member when in said open position.

5. The instrument of claim 4, wherein said backstop comprises at least one wing member which extends away from said backstop shaft when in its open position, and is positioned against or within said backstop shaft when in its closed position.

6. The instrument of claim 5, wherein said backstop includes a pair of said wing members positioned on said backstop shaft.

7. The instrument of claim 5, wherein said penetration member includes at least one cutting blade, and a shaft, and wherein said backstop shaft is slidably positioned at least partially within the shaft of said penetration member such that the shaft of said penetration member may slide along the exterior of said backstop shaft, with said wing member aligned with said cutting blade.

8. The instrument of claim 4, wherein said backstop assembly further includes a rod slidably positioned within said backstop shaft, said rod slidably responsive to the movement of said backstop between said open and closed positions.

9. The instrument of claim 8, wherein said rod is configured such that as said backstop moves from its open to its closed position, said rod will be urged away from said backstop.

10. The instrument of claim 6, wherein said penetration member has a pair of cutting blades positioned at a distal end of the shaft of said penetration member, said backstop shaft positioned at least partially within the shaft of said penetration member such that each of the cutting blades is aligned with one of said wing members.

11. The instrument of claim 10, wherein said penetration member is configured such that it may be slidingly urged along said backstop shaft towards said wing members until said cutting blades contact said wing members.

12. The instrument of claim 5, wherein said wing member is provided at a distal end of said backstop shaft, and wherein said wing member is configured such that as the distal end of the backstop shaft is urged through a layer of tissue, said wing member will be forced to its closed position, and said wing member will return to its closed position after the wing member has passed through the tissue layer.

13. The instrument of claim 12, wherein said backstop assembly is spring-biased toward said penetration member after said wing member moves from its closed to its open position.

14. The instrument of claim 12, wherein said backstop assembly is configured such that at least one of a visible and a audible indicia is produced upon the return of said wing member from its closed to its open position.

15. The instrument of claim 2, further including a housing, said backstop shaft extending at least partially through the interior of said housing, and an advancement member configured for advancing said penetration member along said backstop shaft.

16. The instrument of claim 15, wherein at least a portion of said backstop shaft is rigidly secured within said housing, and wherein said penetration member is releasably secured within said housing, such that said penetration member may not be advanced towards along said backstop shaft until the penetration member has been released.

17. The instrument of claim 16, wherein said backstop assembly and said penetration member are configured such that said penetration member will be released upon movement of said backstop from its closed positioned to its open position.

18. The instrument of claim 17, wherein said penetration member is configured such that, once released and advanced at least partially towards said backstop, said penetration member is prevented from moving away from said backstop.

19. The instrument of claim 18, further comprising at least one latch member configured for releasably securing said penetration member within said housing.

20. The instrument of claim 19, wherein said backstop is movable between open and closed positions, and said backstop is configured such that said backstop will limit the depth of penetration of said penetration member when in said open position, and wherein said latch member is configured to release said penetration member upon movement of said backstop between its closed and open positions.

21. The instrument of claim 2, further comprising a cannula, wherein at least a portion of said penetration member is positioned within said cannula.

22. The instrument of claim 21, wherein said penetration member and said cannula are sized and configured such that said penetration member can be employed to create a tissue opening, through which said cannula may be urged.

23. A trocar for penetrating the tissue wall of an anatomical cavity, comprising:
 (a) a cannula;
 (b) a backstop assembly having a backstop, said backstop assembly positioned at least partially within said cannula; and
 (c) a cutting blade assembly slidably positioned at least partially within said cannula;
wherein said backstop may be urged through a tissue wall into an underlying anatomical cavity, and thereafter a distal end of said cutting blade assembly may be urged through the tissue wall towards said backstop.

24. The trocar of claim 23, wherein said cannula comprises a hollow shaft having proximal and distal ends, and a handle portion positioned at the proximal end of said shaft.

25. The trocar of claim 24, wherein said cannula is spring-biased towards said backstop.

26. The trocar of claim 25, wherein said cannula is releasably retained in a fixed relationship to said backstop assembly.

27. The trocar of claim 26, wherein said cannula is configured such that the cannula will be released from said fixed relationship once said backstop has entered the anatomical cavity.

28. The trocar of claim 23, wherein said backstop assembly further includes a shaft, and said backstop is provided at a distal end of said backstop shaft.

29. The trocar of claim 23, wherein said cutting blade assembly has a distal end and at least one cutting blade positioned at said distal end, and wherein said cutting blade assembly is releasably retained at least partially within said cannula, with said cutting blade positioned within said cannula.

30. The trocar of claim 29, wherein said cutting blade assembly is releasably retained such that said distal end of the cutting blade assembly cannot be urged through a tissue wall until after said backstop is positioned within an anatomical cavy underlying the tissue wall.

31. A method of penetrating the tissue wall of an anatomical cavity, comprising:
 (a) positioning a backstop within the anatomical cavity;
 (b) urging a penetration member through the tissue wall of said cavity towards said backstop.

32. The method of claim 31, wherein said backstop is provided at the distal end of a backstop shaft, and said positioning step comprises urging the distal end of said shaft through said tissue into said cavity.

33. The method of claim 32, wherein said penetration member is urged through said tissue wall along said backstop shaft.

34. The method of claim 33, wherein said penetration member comprises a shaft having distal and proximal ends, and at least one cutting blade positioned at the distal end of the shaft of the penetration member, and wherein said step of urging said penetration member through said tissue wall comprises slidingly urging the shaft of said penetration member along the exterior of said backstop shaft towards the distal end of said backstop shaft.

35. The method of claim 34, wherin said backstop shaft is non-rotatingly, and slidably positioned at least partially within the shaft of said penetration member, and wherein said cutting blade is aligned with said backstop.

36. The method of claim 31, wherein said penetration member has at least one cutting blade, and wherein said penetration member is urged through the tissue wall into said cavity until said cutting blade contacts said backstop.

37. The method of claim 32, wherein said backstop comprises at least one wing member which is movable between an open position whereat said wing member extends away from said shaft, and a closed position whereat said wing member is positioned against or within said backstop shaft, and wherein said distal end of the backstop shaft is urged through said tissue with said wing member in its closed position, and said wing member moves to its open position after said wing member enters said cavity.

38. A method of penetrating the wall of an anatomical cavity, comprising:
 (a) providing a backstop positioned at one end of a backstop shaft, and a penetration member;
 (b) urging at least a portion of said backstop shaft through said wall such that said backstop is positioned within said anatomical cavity, said wall having exterior and interior surfaces;
 (c) providing traction on said backstop shaft so that said backstop is urged against the interior surface of said wall, thereby delineating the location of said interior surface of the wall; and
 (d) urging said penetration member through said wall, while directing the depth of penetration by means of said backstop.

39. The method of claim 38, wherein said penetration member has a distal end and at least one cutting blade at said distal end, and wherein the distal end of said penetration member is urged through said wall only until said cutting blade has passed through said interior surface of said wall.

* * * * *

UNITED STATES PATENT AND TRADEMARK OFFICE
CERTIFICATE OF CORRECTION

PATENT NO. : 6,030,402
DATED : February 29, 2000
INVENTOR(S) : Ronald J. Thompson and Jack B. Stubbs It is certified that error appears in the above-identified patent and that said Letters Patent is hereby corrected as shown below:

Claim 30, column 33, line 55, replace "cavy", with --cavity--.

Signed and Sealed this

Nineteenth Day of December, 2000

Attest:

Q. TODD DICKINSON

*Attesting Officer*        *Commissioner of Patents and Trademarks*